(12) United States Patent
Roberts et al.

(10) Patent No.: US 12,377,291 B2
(45) Date of Patent: Aug. 5, 2025

(54) LIGHT DETECTION APPARATUS AND METHODS FOR A RADIOTHERAPY SYSTEM

(71) Applicant: Elekta Limited, Crawley (GB)

(72) Inventors: David Roberts, Crawley (GB); John Allen, West Sussex (GB)

(73) Assignee: Elekta Limited, Crawley (GB)

( * ) Notice: Subject to any disclaimer, the term of this patent is extended or adjusted under 35 U.S.C. 154(b) by 208 days.

(21) Appl. No.: 17/998,446

(22) PCT Filed: May 11, 2021

(86) PCT No.: PCT/EP2021/062464
§ 371 (c)(1),
(2) Date: Nov. 10, 2022

(87) PCT Pub. No.: WO2021/228845
PCT Pub. Date: Nov. 18, 2021

(65) Prior Publication Data
US 2023/0173305 A1  Jun. 8, 2023

(30) Foreign Application Priority Data

May 12, 2020  (GB) ..................................... 2006943

(51) Int. Cl.
*A61N 5/10* (2006.01)
(52) U.S. Cl.
CPC ......... *A61N 5/1075* (2013.01); *A61N 5/1071* (2013.01); *A61N 2005/1059* (2013.01)

(58) Field of Classification Search
CPC ....................................................... G01T 1/22
See application file for complete search history.

(56) References Cited

U.S. PATENT DOCUMENTS

2010/0265078 A1* 10/2010 Friedman ................ H01J 47/08
340/600
2014/0114150 A1* 4/2014 Pogue .................. A61B 5/1455
600/323

(Continued)

FOREIGN PATENT DOCUMENTS

EP      2708919 A2    3/2014
GB      2538260 A    11/2016

(Continued)

OTHER PUBLICATIONS

"International Application Serial No. PCT/EP2021/062464, International Search Report dated Oct. 11, 2021", (Oct. 11, 2021), 7 pgs.

(Continued)

*Primary Examiner* — David J Makiya
*Assistant Examiner* — Soorena Kefayati
(74) *Attorney, Agent, or Firm* — Schwegman Lundberg & Woessner. P.A.

(57) ABSTRACT

Systems and methods are disclosed for detecting Cherenkov radiation produced during radiotherapy. A radiotherapy system comprises a patient receiving space for receiving a patient, a therapeutic radiation source, and a light detector configured to detect Cherenkov radiation subsequent to the emission of therapeutic radiation. Optionally, the system may make use of a optically transmissive dielectric to produce Cherenkov radiation.

18 Claims, 16 Drawing Sheets

(56) References Cited

U.S. PATENT DOCUMENTS

Figure 1:
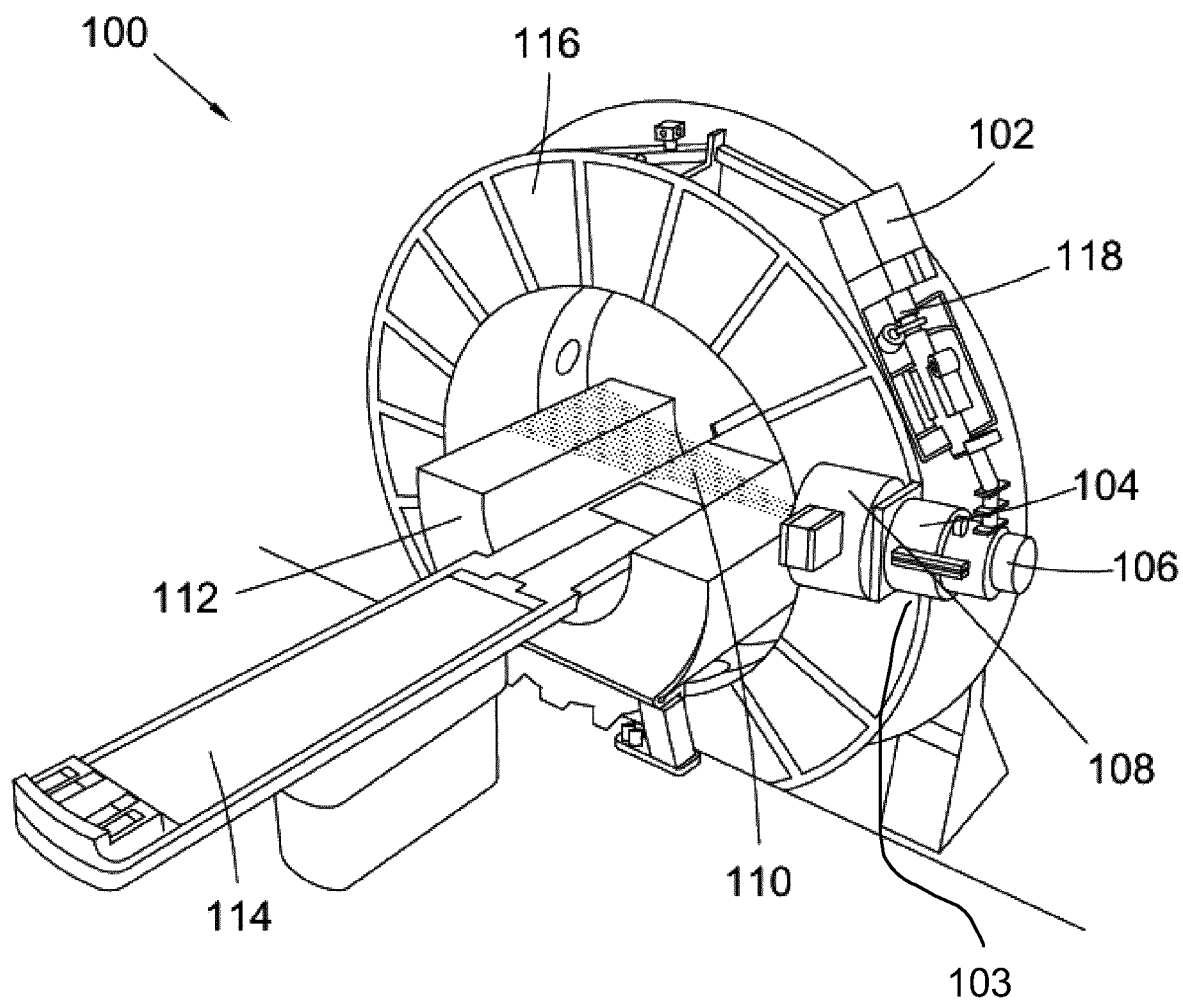

| | | | | |
|---|---|---|---|---|
| 2016/0263402 A1* | 9/2016 | Zhang | ............... | A61N 5/1049 |
| 2017/0252579 A1* | 9/2017 | Kilby | ................ | A61N 5/1071 |
| 2018/0311355 A1* | 11/2018 | Oldham | ............ | A61K 33/244 |
| 2019/0175950 A1* | 6/2019 | Nagumo | ............ | G01T 1/2023 |
| 2020/0061391 A1* | 2/2020 | Krishnaswamy | .... | A61N 5/1071 |
| 2020/0114172 A1* | 4/2020 | Ueno | .................... | G01T 1/023 |

FOREIGN PATENT DOCUMENTS

| | | |
|---|---|---|
| WO | WO-2017211331 A1 | 12/2017 |
| WO | WO-2018076004 A1 | 4/2018 |

OTHER PUBLICATIONS

"International Application Serial No. PCT/EP2021/062464, Written Opinion dated Oct. 11, 2021", (Oct. 11, 2021), 12 pgs.

"United Kingdom Application Serial No. 2006943.1, Examination Report dated Nov. 11, 2020", (Nov. 11, 2020), 7 pgs.

Glaser, Adam K., et al., "Time-gated Cherenkov emission spectroscopy from linear accelerator irradiation of tissue phantoms", Optics letters 37.7, (2012), 1193-1195.

"United Kingdom Application Serial No. 2006943.1, Examination Report dated Dec. 7, 2022", 1 pg.

\* cited by examiner

900

Using a therapeutic radiation source of a radiotherapy system to irradiate an optically transmissive dielectric with therapeutic radiation S901

Detecting, at a light detector, Cherenkov radiation emitted by the optically transmissive dielectric S902

1200

```
Control, during a radiotherapy or
calibration session, a therapeutic
radiation source to cause
emission of a series of pulses of
therapeutic radiation towards a
patient receiving space S1201
            │
            ▼
Operate a light detector to detect
Cherenkov radiation during a
series of detection windows
S1203
            │
            ▼
Operate the light detector so
that, between adjacent detection
windows, the light detector is not
able to detect Cherenkov
radiation S1205
```

Fig. 12

LIGHT DETECTION APPARATUS AND METHODS FOR A RADIOTHERAPY SYSTEM

PRIORITY APPLICATIONS

This application is a U.S. National Stage Filing under 35 U.S.C. § 371 from International Application No. PCT/EP2021/062464, filed on May 11, 2021, and published as WO2021/228845 on Nov. 18, 2021, which claims the benefit of priority to United Kingdom Application No. 2006943.1, filed on May 12, 2020; the benefit of priority of each of which is hereby claimed herein, and which applications and publication are hereby incorporated herein by reference in their entireties.

This disclosure relates to apparatus, devices, systems, computer readable media, and approaches for radiotherapy, and in particular but without limitation to systems, methods and computer readable media for detecting Cherenkov radiation produced by such a system.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour.

For effective treatment and treatment plan quality assurance (QA), it is preferential to estimate or measure the radiation dose delivered to the patient. The disclosure below is described with reference to quality assurance, but the systems, apparatuses, and methods disclosed herein may equally be applied to calibration and/or initial set up of a radiotherapy system.

There are many possible technologies for detecting radiation, such as ion chambers and many types of solid-state detector. However, those detectors are based on individual detector elements, which can be made into area-based pixel detectors, but the complexity and cost generally increases such that it is only feasible to have a limited number of detectors at a limited number of positions.

The present disclosure seeks to address these and other disadvantages encountered in the prior art.

SUMMARY

An invention is set out in the claims.

FIGURES

Figure 2:
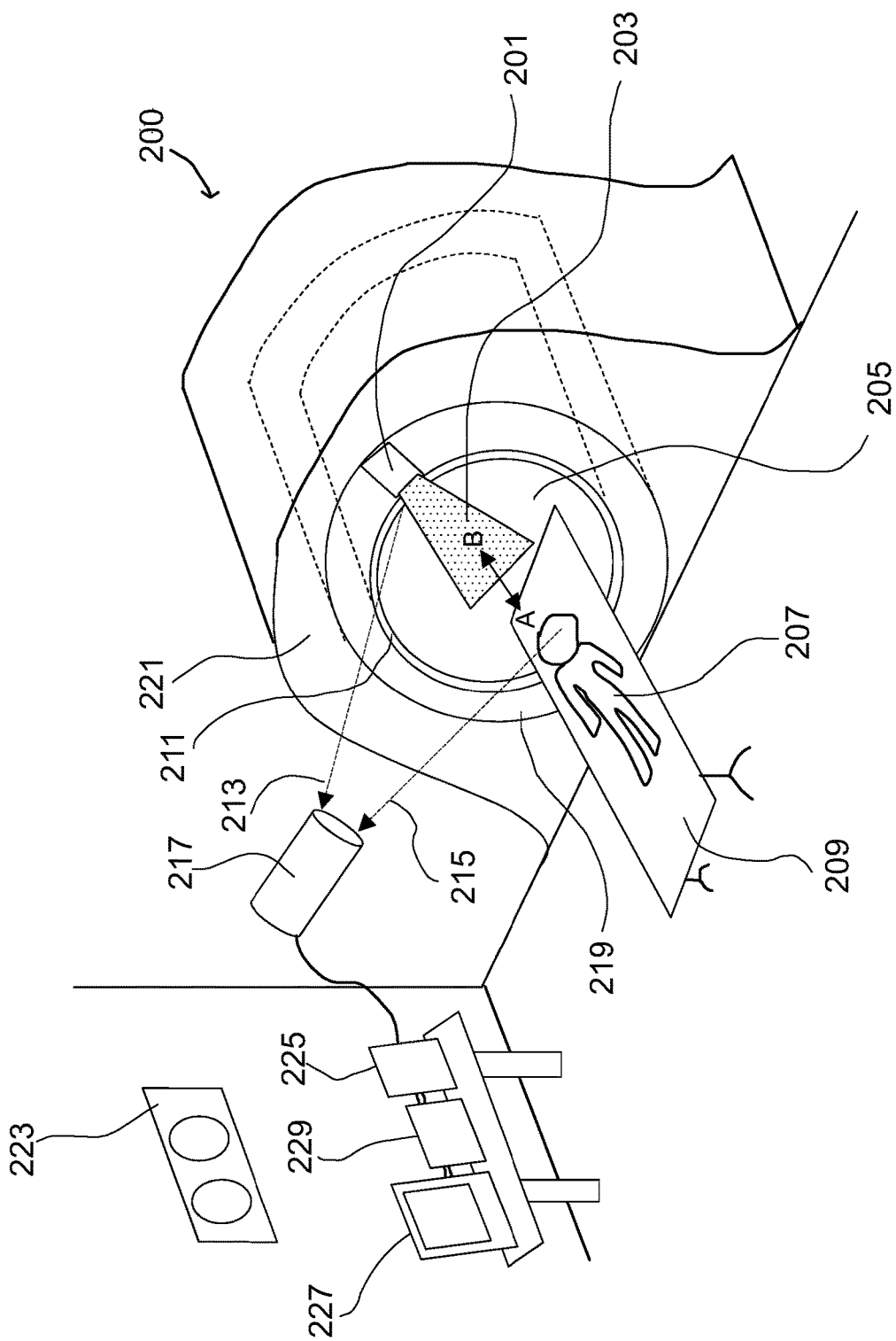
Figure 3:
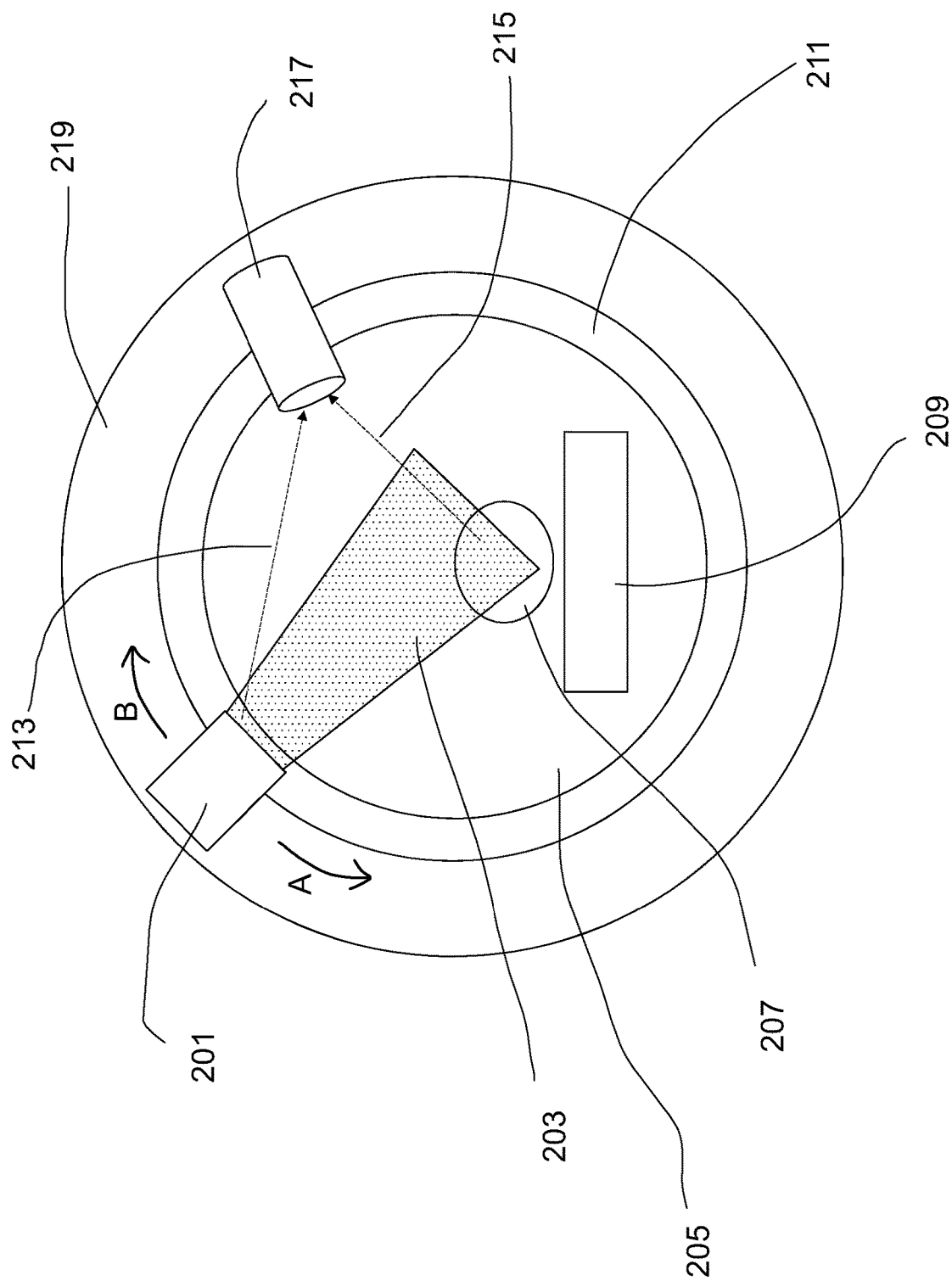
Figure 4:
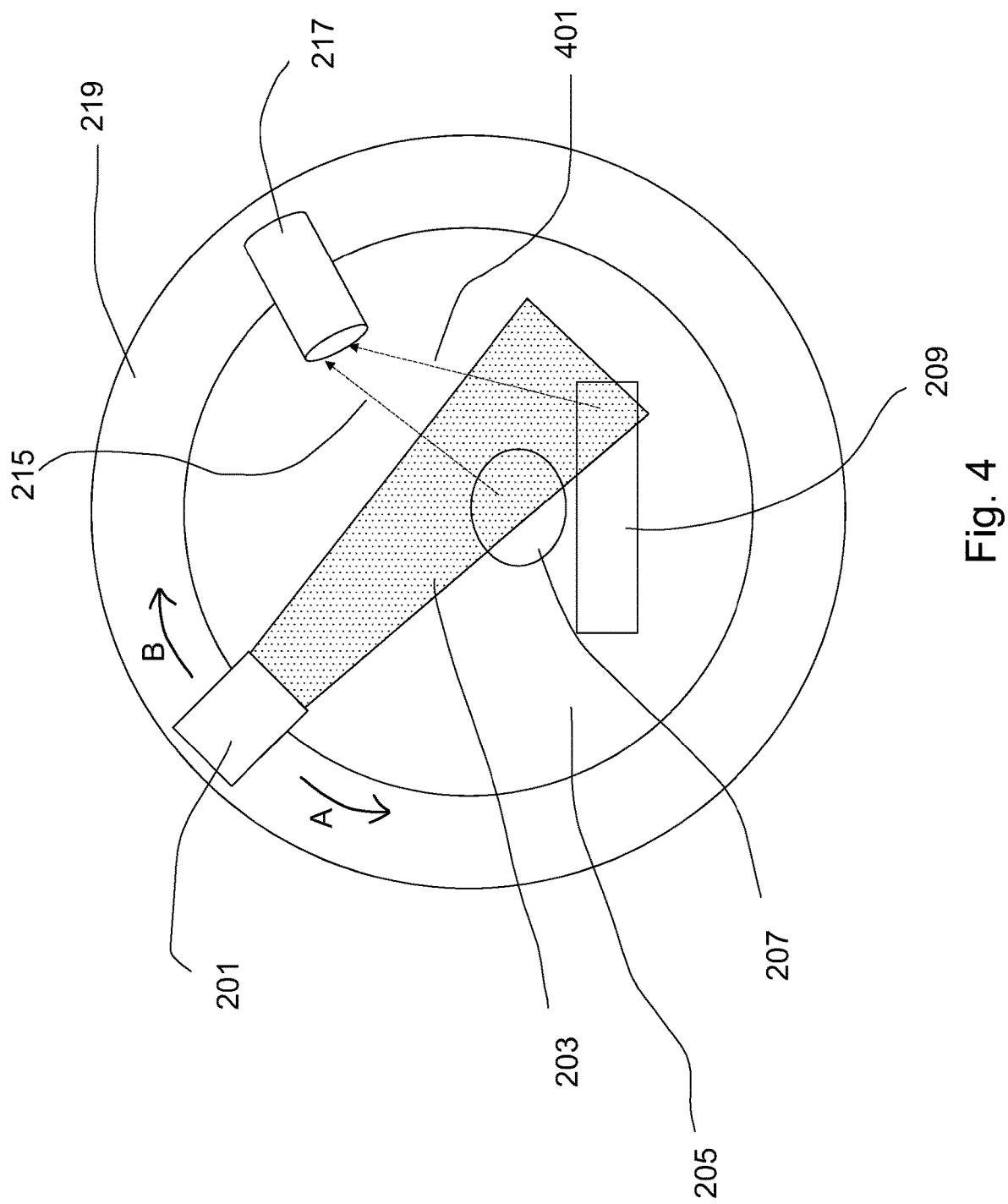
Figure 5:
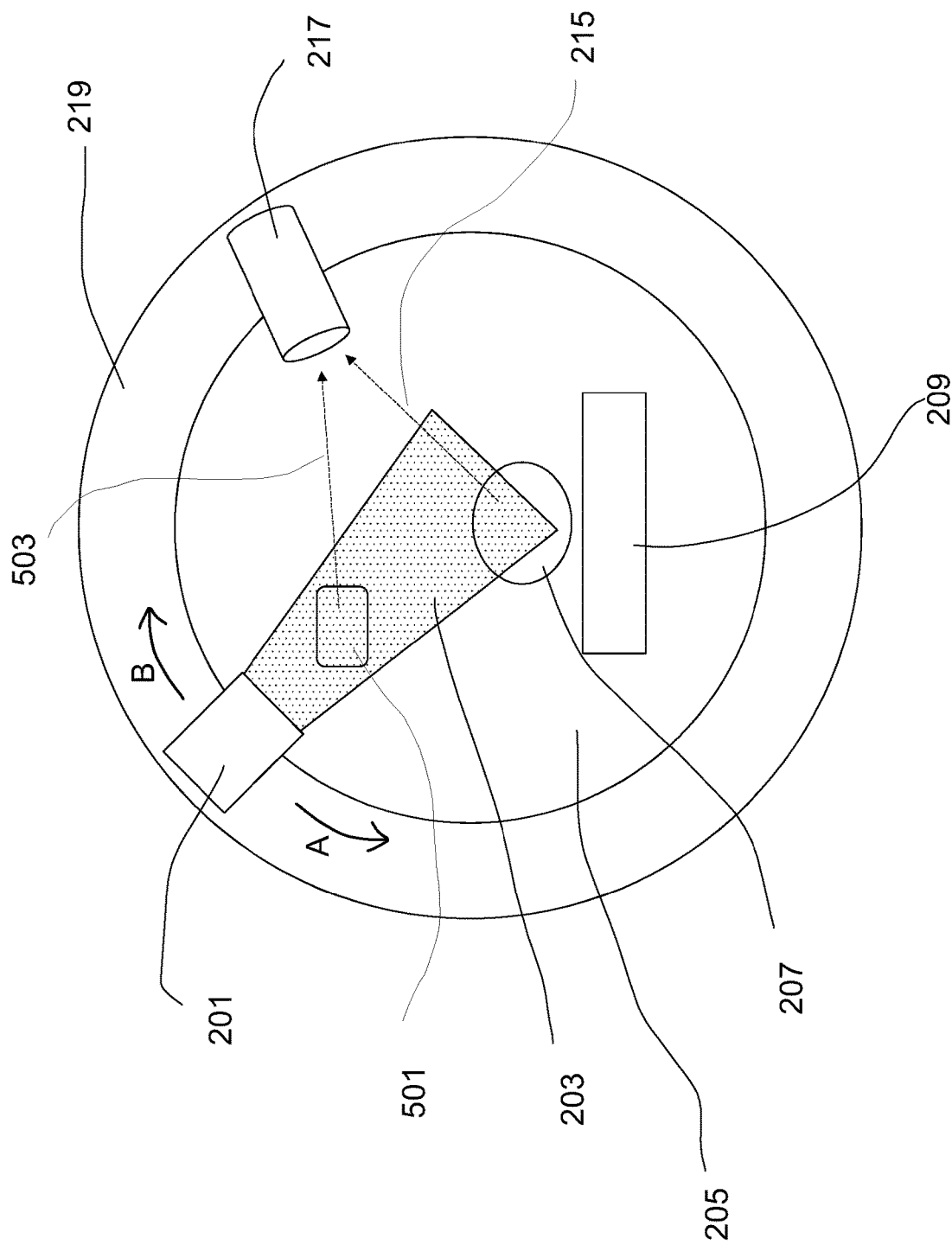
Figure 6:
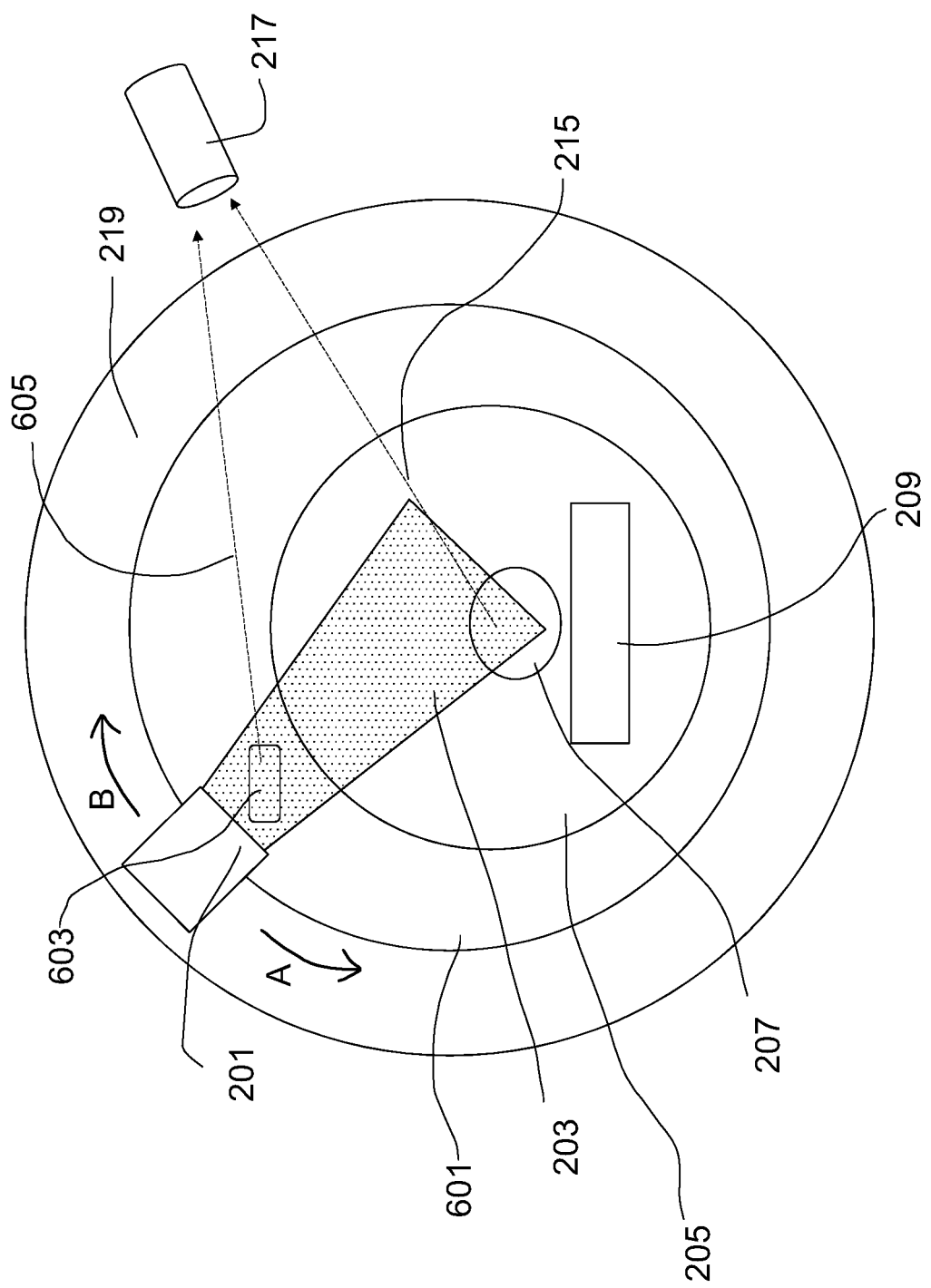
Figure 7:
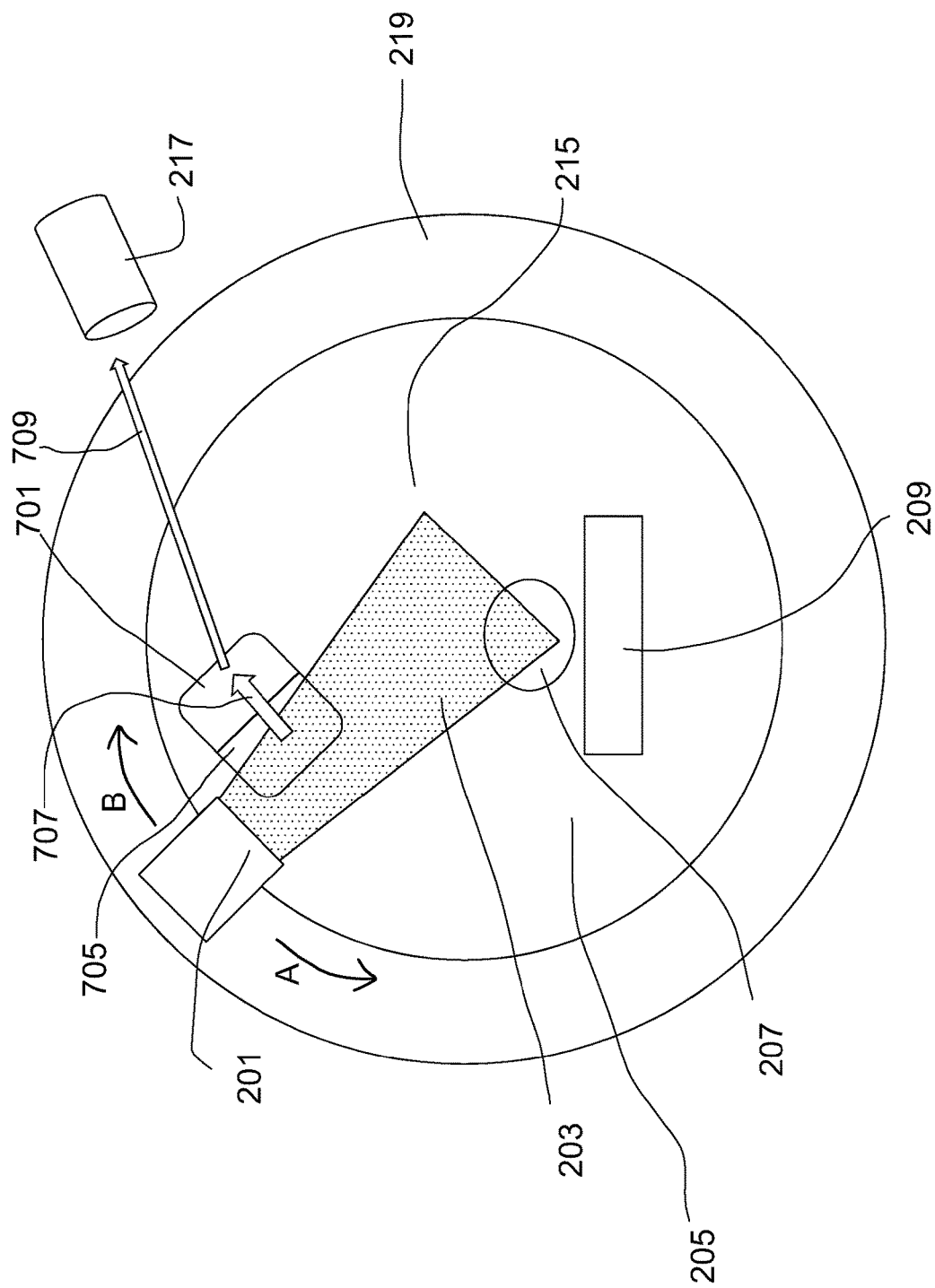
Figure 8:
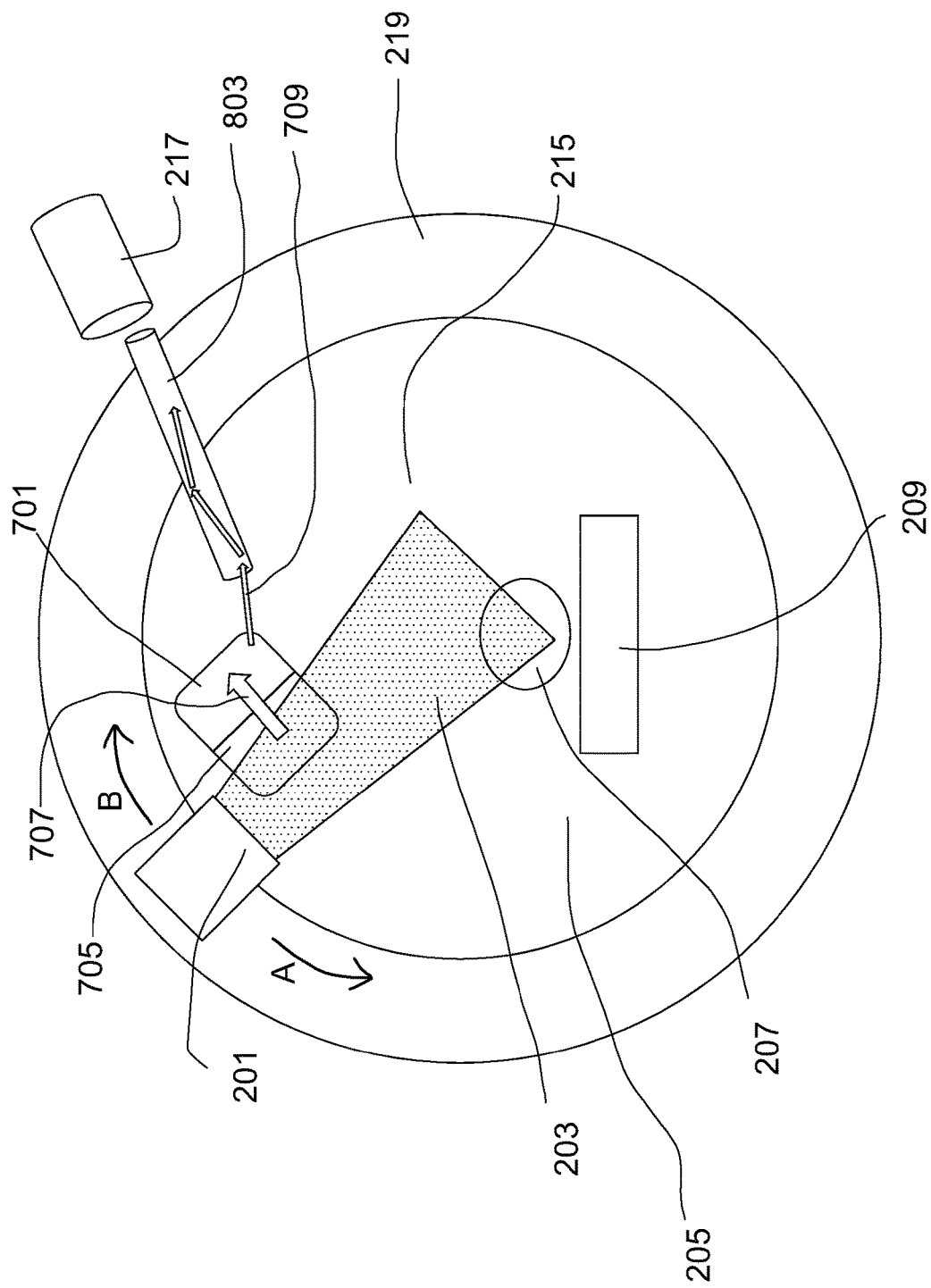
Figure 9:
Figure 10:
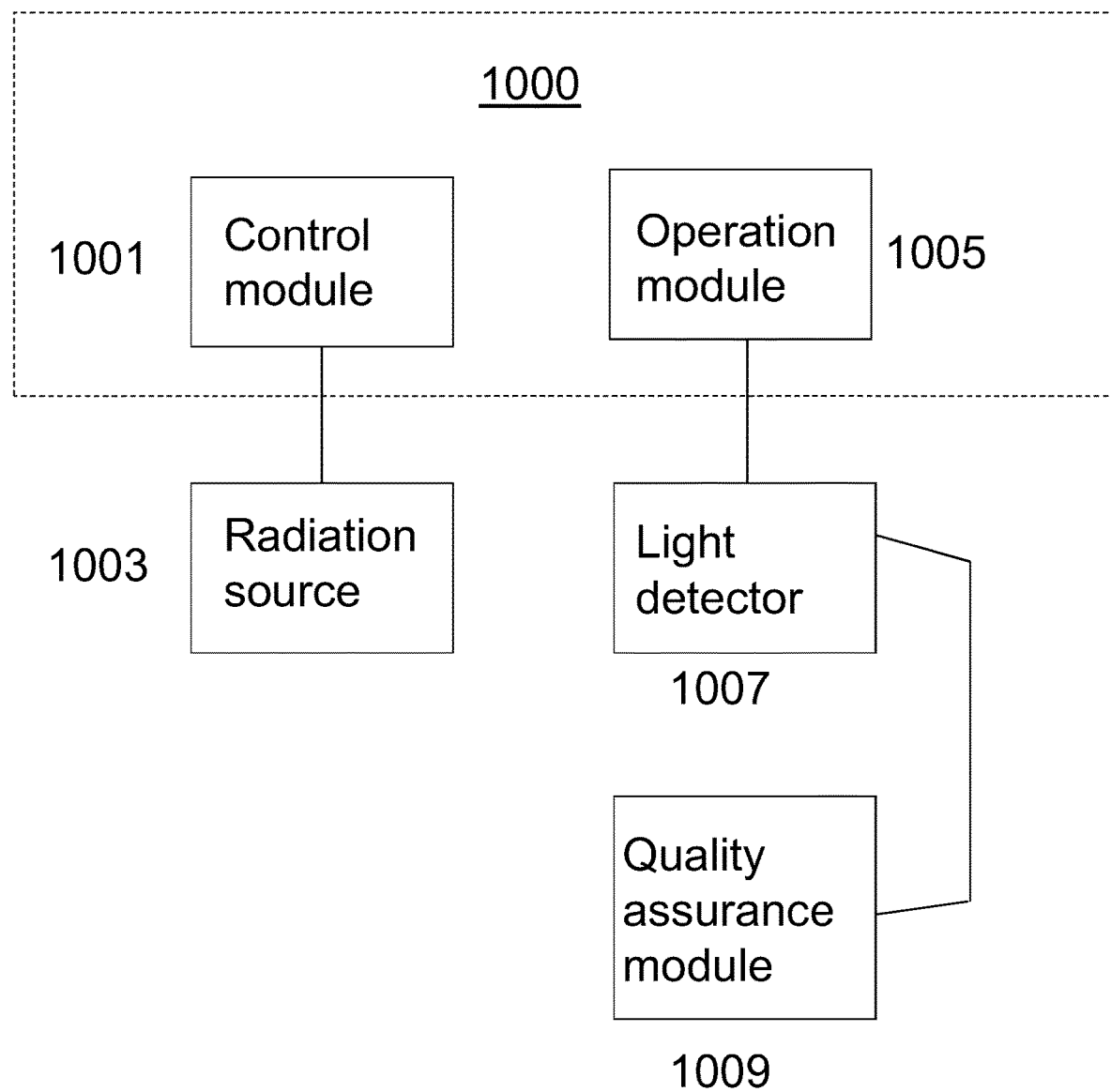
Figure 11:
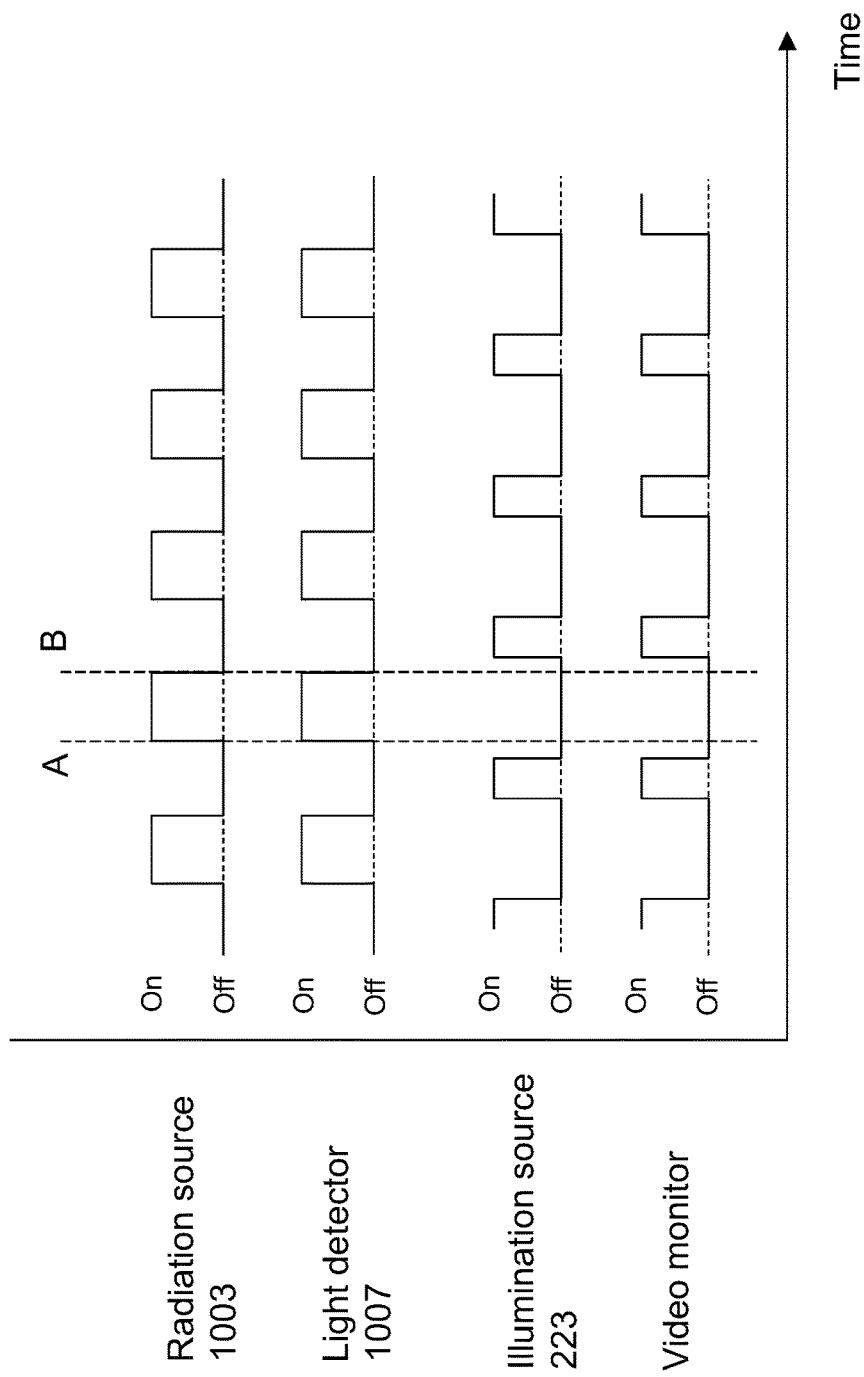
Figure 13:
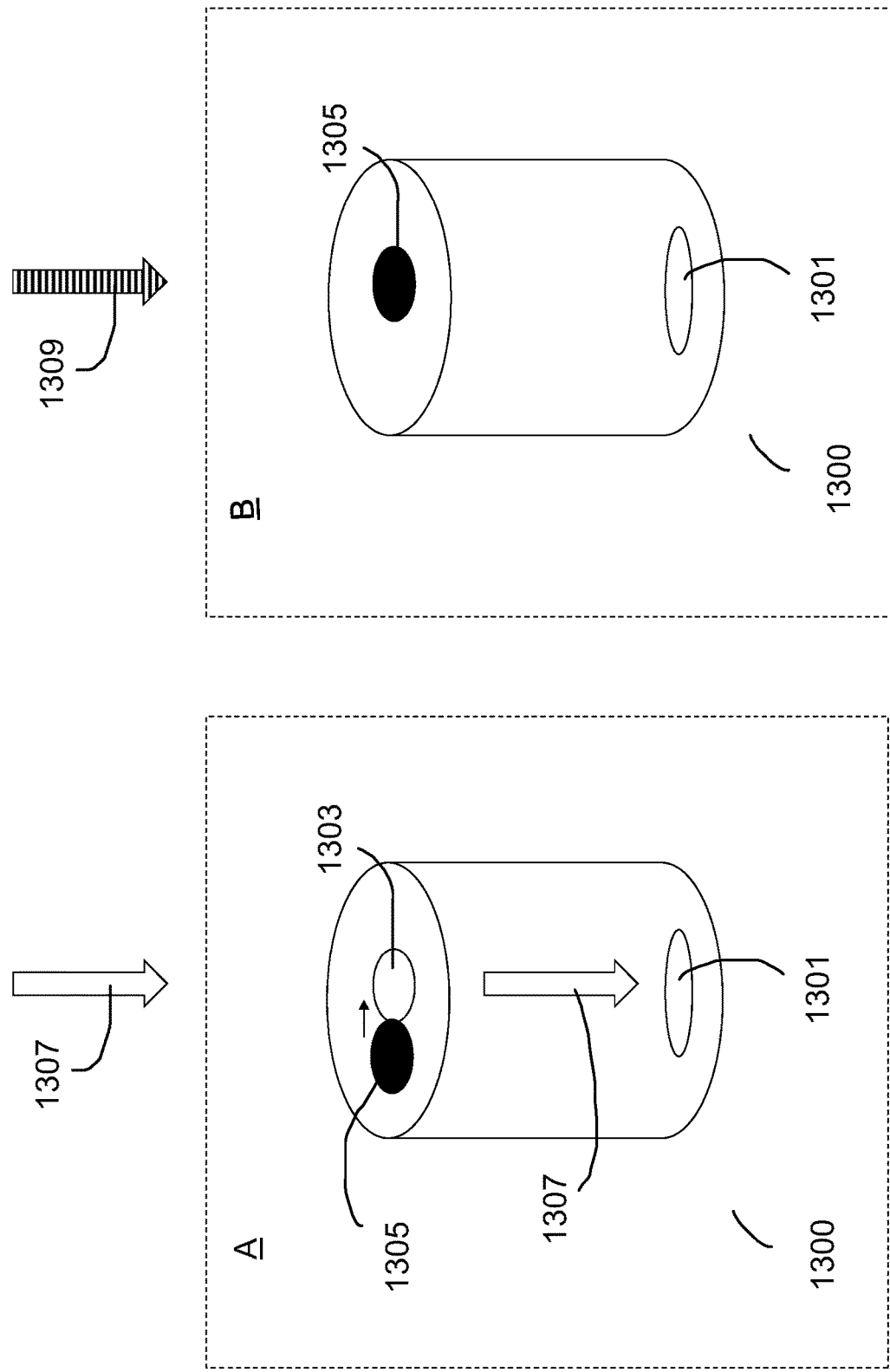
Figure 14:
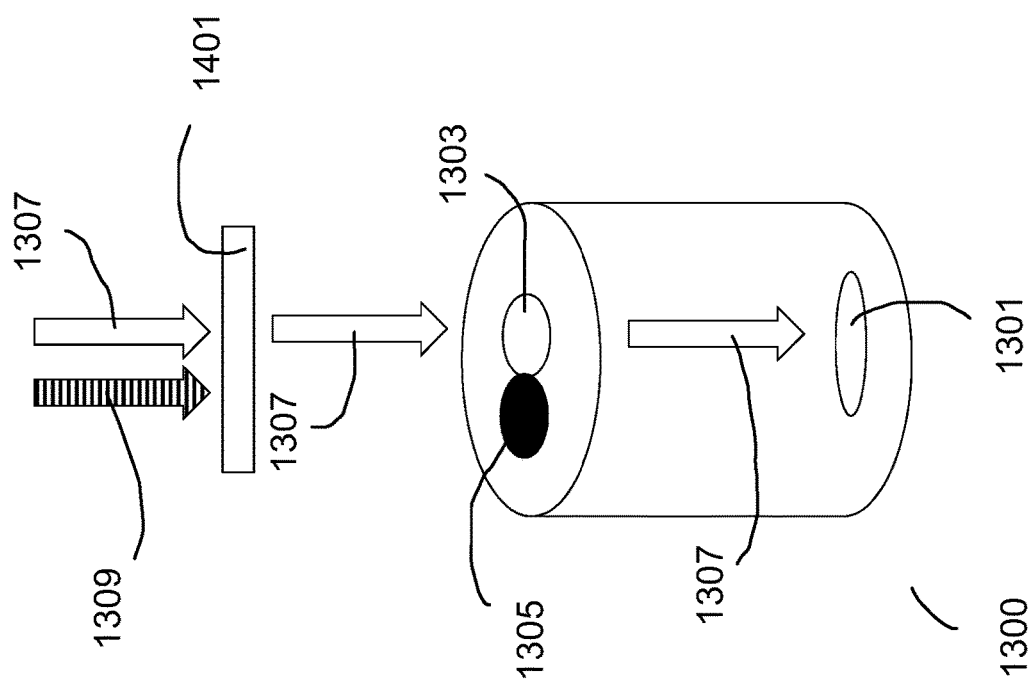
Figure 15:
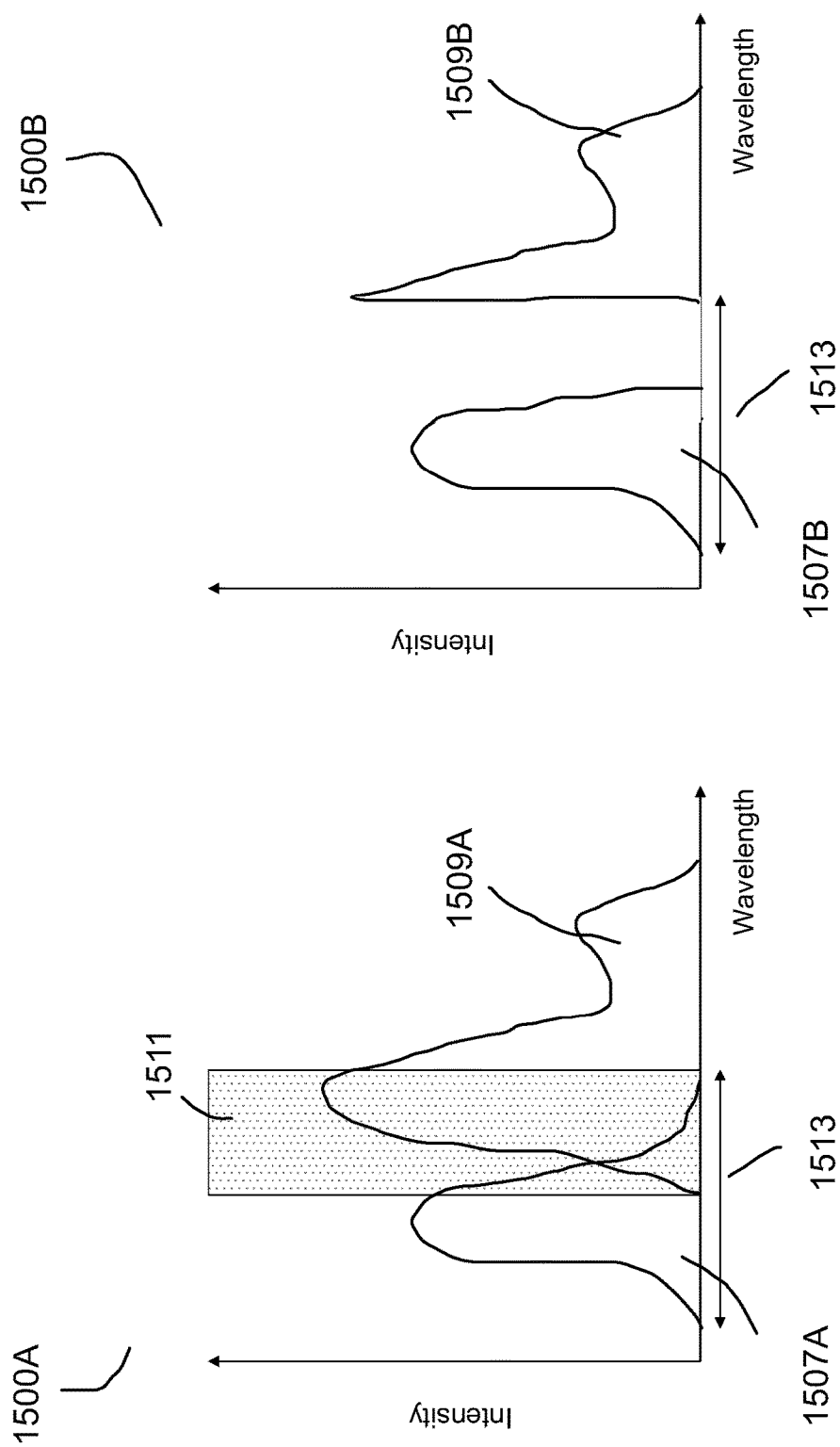
Figure 16:
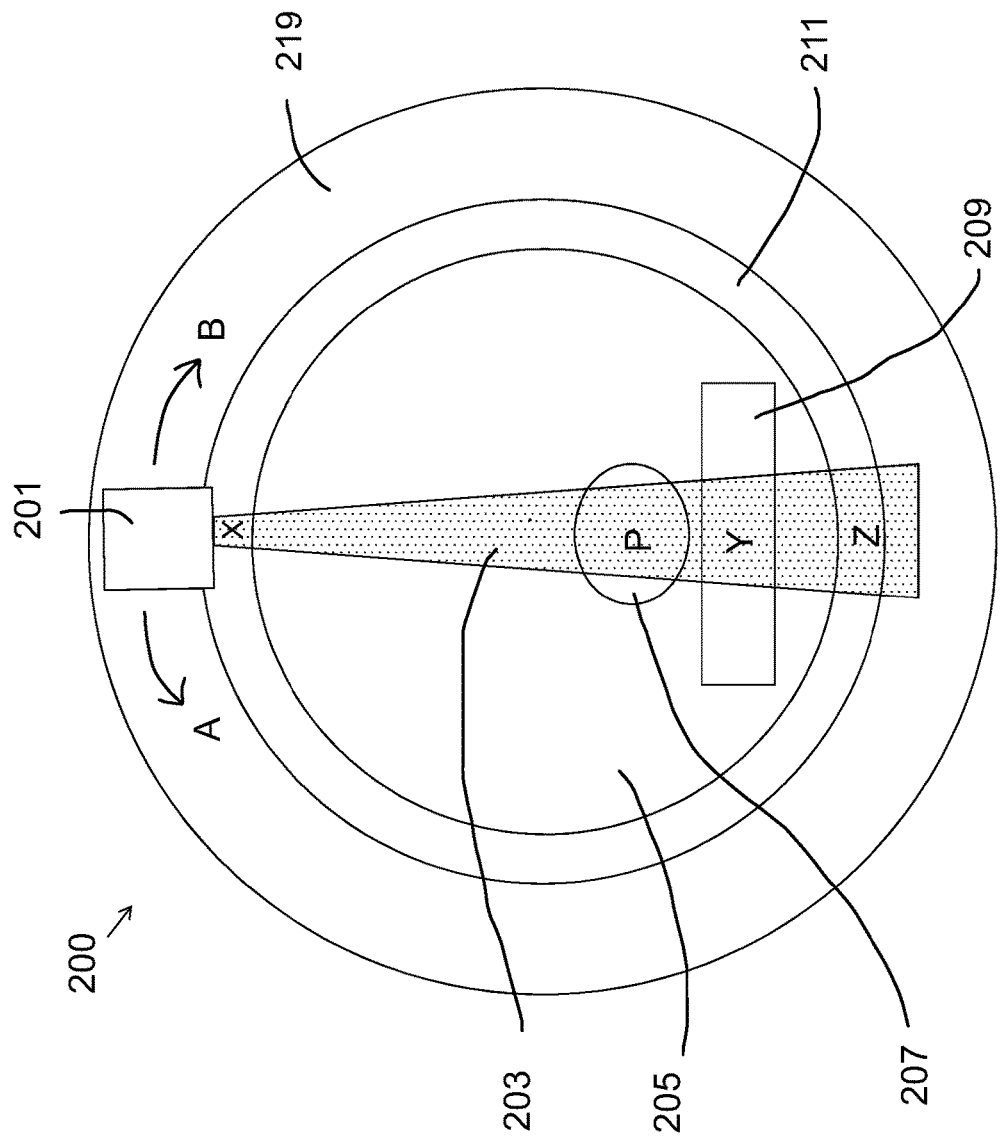

Specific examples are now described, by way of example only, with reference to the drawings, in which:

FIG. 1 shows a radiotherapy device or system;
FIG. 2 shows a system for detecting Cherenkov radiation;
FIG. 3 shows a cross-section of a system for detecting Cherenkov radiation;
FIG. 4 shows a cross-section of a system for detecting Cherenkov radiation;
FIG. 5 shows a cross-section of a system for detecting Cherenkov radiation;
FIG. 6 shows a cross-section of a system for detecting Cherenkov radiation;
FIG. 7 shows a cross-section of a system for detecting Cherenkov radiation;
FIG. 8 shows a cross-section of a system for detecting Cherenkov radiation;
FIG. 9 shows a method for detecting Cherenkov radiation;
FIG. 10 shows a control module and an operation module;
FIG. 11 shows a pulse timing diagram;
FIG. 12 shows a method of controlling and operating a system;
FIG. 13 shows a light detector for detecting Cherenkov radiation;
FIG. 14 shows a light detector for detecting Cherenkov radiation;
FIG. 15 shows example spectra of Cherenkov radiation and room illumination; and
FIG. 16 shows a cross-section of a system for detecting Cherenkov radiation.

DETAILED DESCRIPTION

In the following description, reference is made to the accompanying drawings, which form a part hereof, and in which show by way of illustration specific embodiments in which the invention may be practiced. It is to be understood that other embodiments may be utilized and structural or logical changes may be made without departing from the scope of the present invention. The following description, therefore, is not to be taken in a limiting sense. It is to be understood that, unless specifically noted otherwise, this disclosure provides that any feature or features of the various example embodiments described herein may be combined, in part or whole, with any other such feature or features and that such combination may occur in the absence of any further such feature or features.

FIG. 1 shows a radiotherapy device suitable for delivering, and configured to deliver, a beam of radiation to a patient during radiotherapy treatment. The device and its constituent components will be described generally for the purpose of providing useful accompanying information for the present disclosure. The device shown in FIG. 1 is in accordance with the present disclosure and is suitable for use with the disclosed systems and apparatuses. While the device in FIG. 1 is an MR-linac (magnetic resonance linear accelerator), the implementations of the present disclosure may be any radiotherapy device, for example a linac (linear accelerator) device.

The device 100 shown in FIG. 1 is an MR-linac. The device 100 comprises both MR imaging apparatus 112 and radiotherapy (RT) apparatus which may comprise a linac device. The MR imaging apparatus 112 is shown in the diagram in a partially cut away perspective manner. In operation, the MR scanner produces MR images of the patient, and the linac device produces and shapes a beam of radiation and directs it towards a target region within a patient's body in accordance with a radiotherapy treatment plan. FIG. 1 does not show the usual 'housing' which would cover the MR imaging apparatus 112 and RT apparatus in a commercial setting such as a hospital.

The MR-linac device shown in FIG. 1 comprises a source 102 of radiofrequency waves, a waveguide 104, a source of electrons 106, a radiation source 103, a collimator 108 such as a multi-leaf collimator configured to collimate and shape the beam, MR imaging apparatus 112 (shown partially cut away), and a patient support surface 114. In use, the device would also comprise a housing (not shown) which, together with the ring-shaped gantry, defines a bore. The patient support surface 114 is moveable and can be used to support a patient and move them, or another subject, into the bore when an MR scan and/or when radiotherapy is to commence. The MR imaging apparatus 112, RT apparatus, and a subject support surface actuator are communicatively coupled to a controller or processor. The controller is also communicatively coupled to a memory device comprising computer-executable instructions which may be executed by the controller.

The RT apparatus comprises a radiation source 103 and a radiation detector (not shown). Typically, the radiation detector is positioned diametrically opposed to the radiation source 103. The radiation detector is suitable for, and configured to, produce radiation intensity data. In particular, the radiation detector is positioned and configured to detect the intensity of radiation which has passed through the subject. The radiation detector may also be described as radiation detecting means, and may form part of a portal imaging system.

The radiation source 103 may comprise a beam generation system. For a linac, the beam generation system may comprise a source 102 of RF waves, an electron gun 106, and a waveguide 104. The radiation source 103 is attached to the rotatable gantry 116 so as to rotate with the gantry 116. In this way, the radiation source 103 is rotatable around the patient so that a treatment beam 110 can be applied from different angles around the gantry 116. In a preferred implementation, the gantry is continuously rotatable. In other words, the gantry can be rotated by 360 degrees around the patient, and in fact may continue to be rotated past 360 degrees. The gantry may be ring-shaped. In other words, the gantry may be a ring-gantry.

The source 102 of radiofrequency waves, such as a magnetron, is configured to produce radiofrequency waves. The source 102 of radiofrequency waves is coupled to the waveguide 104 via a circulator 118 and is configured to pulse radiofrequency waves into the waveguide 104. Radiofrequency waves may pass from the source 102 of radiofrequency waves through an RF input window and into an RF input connecting pipe or tube. An electron source 106, such as an electron gun, is also coupled to the waveguide 104 and is configured to inject electrons into the waveguide 104. In the electron source 106, electrons are thermionically emitted from a cathode filament as the filament is heated. The temperature of the filament controls the number of electrons injected. The injection of electrons into the waveguide 104 is synchronised with the pumping of the radiofrequency waves into the waveguide 104. The design and operation of the source 102 of radiofrequency waves, electron source 106 and the waveguide 104 is such that the radiofrequency waves accelerate the electrons to very high energies as the electrons propagate through the waveguide 104.

The design of the waveguide 104 depends on whether the linac accelerates the electrons using a standing wave or travelling wave, though the waveguide typically comprises a series of cells or cavities, each cavity connected by a hole or 'iris' through which the electron beam may pass. The cavities are coupled in order that a suitable electric field pattern is produced which accelerates electrons propagating through the waveguide 104. As the electrons are accelerated in the waveguide 104, the electron beam path is controlled by a suitable arrangement of steering magnets, or steering coils, which surround the waveguide 104. The arrangement of steering magnets may comprise, for example, two sets of quadrupole magnets.

Once the electrons have been accelerated, they may pass into a flight tube. The flight tube may be connected to the waveguide by a connecting tube. This connecting tube or connecting structure may be called a drift tube. The electrons travel toward a heavy metal target which may comprise, for example, tungsten. Whilst the electrons travel through the flight tube, an arrangement of focusing magnets act to direct and focus the beam on the target.

To ensure that propagation of the electrons is not impeded as the electron beam travels toward the target, the waveguide 104 is evacuated using a vacuum system comprising a vacuum pump or an arrangement of vacuum pumps. The pump system is capable of producing ultra-high vacuum (UHV) conditions in the waveguide 104 and in the flight tube. The vacuum system also ensures UHV conditions in the electron gun. Electrons can be accelerated to speeds approaching the speed of light in the evacuated waveguide 104.

The radiation source 103 is configured to direct the treatment beam 110 of therapeutic radiation toward a patient positioned on the patient support surface 114. The radiation source 103 may therefore also be referred to as a therapeutic radiation source. The radiation source 103 may comprise a heavy metal target towards which the high energy electrons exiting the waveguide are directed. When the electrons strike the target, X-rays are produced in a variety of directions. A primary collimator may block X-rays travelling in certain directions and pass only forward travelling X-rays to produce the treatment beam 110. The X-rays may be filtered and may pass through one or more ion chambers for dose measuring. The beam can be shaped in various ways by beam-shaping apparatus, for example by using the multi-leaf collimator 108, before it passes into the patient as part of radiotherapy treatment.

In some implementations, the radiation source 103 is configured to emit either an X-ray beam or an electron particle beam. Such implementations allow the device to provide electron beam therapy, i.e. a type of external beam therapy where electrons, rather than X-rays, are directed toward the target region as the therapeutic radiation. It is possible to 'swap' between a first mode in which X-rays are emitted and a second mode in which electrons are emitted by adjusting the components of the linac. In essence, it is possible to swap between the first and second mode by moving the heavy metal target in or out of the electron beam path and replacing it with a so-called 'electron window'. The electron window is substantially transparent to electrons and allows electrons to exit the flight tube.

The subject or patient support surface 114 is configured to move between a first position substantially outside the bore, and a second position substantially inside the bore. In the first position, a patient or subject can mount the patient support surface. The patient support surface 114, and patient, can then be moved inside the bore, to the second position, in order for the patient to be imaged by the MR imaging apparatus 112 and/or imaged or treated using the RT apparatus. The bore may hence lie about a portion of space that is suitable for receiving at least a portion of a patient—a patient receiving space. The movement of the patient support surface is effected and controlled by a subject support surface actuator, which may be described as an actuation mechanism. The actuation mechanism is configured to move the subject support surface in a direction parallel to, and defined by, the central axis of the bore. The terms subject and patient are used interchangeably herein such that the subject support surface can also be described as a patient support surface. The subject support surface may also be referred to as a moveable or adjustable couch or table.

The radiotherapy apparatus/device shown in FIG. 1 also comprises MR imaging apparatus 112. The MR imaging apparatus 112 is configured to obtain images of a subject positioned, i.e. located, on the patient support surface 114.

The MR imaging apparatus 112 may also be referred to as the MR imager. The MR imaging apparatus 112 may be a conventional MR imaging apparatus operating in a known manner to obtain MR data, for example MR images. The skilled person will appreciate that such a MR imaging apparatus 112 may comprise a primary magnet, one or more gradient coils, one or more receive coils, and an RF pulse applicator.

The operation of the MR imaging apparatus is controlled by the controller.

The controller is a computer, processor, or other processing apparatus. The controller may be formed by several discrete processors; for example, the controller may comprise an MR imaging apparatus processor, which controls the MR imaging apparatus 110; an RT apparatus processor, which controls the operation of the RT apparatus; and a subject support surface processor which controls the operation and actuation of the patient support surface. The controller is communicatively coupled to a memory, e.g. a computer readable medium.

The linac device also comprises several other components and systems as will be understood by the skilled person. For example, in order to ensure the linac does not leak radiation, appropriate shielding is also provided.

One possible approach for the indirect detection of radiation and that has potential for QA is the measurement of Cherenkov radiation. Cherenkov radiation is produced when charged particles travel through an optical medium (such as a patient's skin or another optically transmissive dielectric material) at a speed greater than the local speed of light. The local speed of light in the medium is usually less than the speed of light in a vacuum, and so an effect analogous to a sonic boom occurs when the charged particle exceeds the local speed of light. When using an x-ray based radiotherapy treatment beam, wherein x-rays are used as therapeutic radiation, x-rays incident on a medium can ionise atoms in the medium, generating secondary electrons with high energy. Cherenkov radiation is produced directly from those high energy electrons as they themselves pass through the medium. When using an electron particle beam for radiotherapy, wherein the electron beam is used as therapeutic radiation, the electrons from the radiotherapy beam itself can create Cherenkov radiation when incident on an appropriate material. In the example system of FIG. 1, therefore, the charged particle producing the Cherenkov radiation is an electron regardless of whether electrons or x-rays are being used for the clinical treatment. To produce electrons that travel at a speed greater than the local speed of light, and thereby create Cherenkov radiation, the energy of the treatment beam needs to be significantly above 1 MeV, which is the case for a typical medical linac.

Although the examples disclosed herein are described by reference to an x-ray-based radiotherapy device for ease of understanding, the systems, apparatuses and methods disclosed herein may also, or alternatively, be applied to proton-based radiation therapy. In proton-based radiation therapy a particle accelerator produces protons for use as therapeutic radiation. The proton acts as a charged particle that will emit Cherenkov radiation when travelling through a medium at a speed greater than the local speed of light.

Cherenkov radiation is usually emitted at visible wavelengths (or near ultra violet) that can be measured with standard camera technology.

Cherenkov radiation can therefore be measured in order to evaluate or monitor the dose delivered by the radiotherapy apparatus, in other words, for dosimetry, quality assurance, and/or calibration purposes. Moreover, a camera can replace complex and costly arrays of detectors that directly detect radiation. However, the level of light produced by Cherenkov radiation is very low compared to the typical level of ambient room lighting. Cherenkov based radiation detection has been demonstrated in and around radiotherapy linacs, but such experiments have been conducted in dark rooms without lighting. When treating a real patient, the idea of the patient having to lie still in a pitch-black room is not conducive to keeping them comfortable. Patient discomfort such as a feeling of claustrophobia, fear, or nerves from being in the dark can cause the patient to move around, causing problems during scanning and dosing. The absence of illumination in such a set up also means that the operator cannot use a video monitoring system that is typically used to check if the patient is comfortable and remaining still during treatment.

In addition to dosimetry, Cherenkov radiation may be used to measure or reconstruct the distribution of the treatment beam, allowing a measurement of three dimensional dose distribution and/or quantity to be made. Using Cherenkov radiation in such a way can therefore provide similar functionality to conventional beam imaging components of a radiotherapy system, including the use of imagers during calibration and set up of radiotherapy systems. Cherenkov radiation is produced asymmetrically by a directional emission process. A cone of radiation is produced as the charged particle travels through the medium. The cone has an angle that is dependent upon the velocity of the particle and the refractive index of the medium. If a beam passes through a medium that subsequently emits Cherenkov radiation then measuring or imaging the direction and/or shape of the Cherenkov radiation with appropriately placed detectors would provide further information about the distribution of the initial radiotherapy beam. In particular, the relative fluence distribution of the beam can be measured. In clinical practice the reference dose is usually quoted as the dose at the centre at a reference depth inside the patient. The reference dose value can either be measured or calculated. If the reference dose value is known, then a fluence value at a point of measurement can be scaled relative to a fluence value in the patient by taking into account both a numerical factor and a geometrical scaling. The geometrical scaling accounts for the fact that the beam is divergent and hence will have larger dimensions in the patient than at a plane of measurement closer to the radiation source.

In some examples, detectors are placed such that Cherenkov radiation can be detected from the radiotherapy beam before it enters the patient and/or from the radiotherapy beam after it has passed through the patient. There are advantages to each option. Measuring the Cherenkov radiation produced by the radiotherapy beam after it has passed through the patient can give an indication of the dose absorbed by the patient, but the estimate may include errors due to the patient geometry. Measuring the Cherenkov radiation produced by the radiotherapy beam before it enters the patient can measure precisely what is emitted by the radiotherapy device before the introduction of any such sources of error.

Cherenkov radiation may also be used for quality assurance purposes by providing a measurement or estimate of a dose being delivered by the radiotherapy system prior to, or after, a radiotherapy session. In other words, Cherenkov radiation may be used to calibrate the dose delivery of a radiotherapy system. Calibration routines may be performed in the absence of a patient or with a patient present. The systems and methods disclosed herein make use of Cherenkov radiation to estimate dose in a way that allows a machine to be calibrated by comparing the estimated dose to previously characterised doses that, for example, were previously measured using the same system or method and were independently verified.

FIG. 2 shows a radiotherapy system 200 suitable for detecting Cherenkov radiation for the purpose of quality assurance. The radiotherapy system comprises a radiotherapy device suitable for delivering, and configured to deliver, a beam of radiation to a patient during radiotherapy treatment, such as the device of FIG. 1.

A therapeutic radiation source 201 is arranged to emit a beam of therapeutic radiation 203 towards a patient receiving space 205. The therapeutic radiation source 201 is arranged to provide therapeutic radiation and may be equivalent to the previously discussed radiation source 103. The patient receiving space 205 is configured to receive a patient 207. The patient receiving space 205 may correspond to the physical space occupied by the patient 207 during treatment. In one example, if the patient 207 were to change position or move during treatment, the definition of the patient receiving space 205 would correspondingly change to be equivalent to the space occupied by the patient in a new position. In one example, the emission of a beam of therapeutic radiation towards the patient receiving space 205 will necessarily also be towards any patient 207 within the patient receiving space 205. Alternatively, the patient receiving space 205 may be a larger space which encloses at least part of the patient 207 within it during treatment as well as having additional space within which additional matter can be arranged. In one example, the patient receiving space 205 is considered to be a fixed space that does not move or change according to the position of the patient 207. In one example, the patient receiving space 205 can be considered a fixed region of space within which radiotherapy is performed. A fixed portion of the patient receiving space may be combined with any additional space occupied by a patient 207 at a particular moment to form the patient receiving space 205. The patient receiving space 205 is a region of space suitable for receiving a patient and that region of space is considered to be the patient receiving space regardless of whether or not a patient 207 is actually present within the space at a given moment in time. The system and methods described herein can be used with a patient present in the patient receiving space 205 or in the absence of a patient. The patient will typically be supported by a support surface or table 209, similar to the patient support surface 114, that can be moved at least partially into and out of the patient receiving space 205.

An optically transmissive dielectric 211 is arranged such that, when a patient is received in the patient receiving space, both the patient and the optically transmissive dielectric can be irradiated by the therapeutic radiation source 201. A dielectric material with optical transparency is chosen for the optically transmissive dielectric 211 in order to allow photons of Cherenkov radiation produced within the optically transmissive dielectric 211 to propagate through the dielectric material and escape the material with minimal attenuation.

As such, the terms transparent and transparency should be interpreted throughout the present disclosure as describing a material that is sufficiently optically transmissive to allow at least some Cherenkov radiation (as may be generated therewithin) to pass therethrough. Any material described as transparent or optically transmissive herein should not be interpreted as a material having perfect or high levels of transparency, nor as limited to materials that are perceived as transparent by the human eye. Indeed, translucent dielectric materials may be used as the optically transmissive dielectric and materials that appear opaque to the human eye but are transmissive of Cherenkov radiation, for example layers of skin, should be considered to be optically transmissive and/or transparent for the purpose of emitting and/or conveying Cherenkov radiation.

Subsequent to escaping the optically transmissive dielectric material, the Cherenkov radiation can be detected or imaged externally. FIG. 2 shows the optically transmissive dielectric 211 as a coating on the outer surface of a bore that partially encloses the patient receiving space 205. The radiation source 201 emits the beam of therapeutic radiation 203 towards the patient receiving space 205 such that the beam of therapeutic radiation 203 passes through the optically transmissive dielectric 211. The optically transmissive dielectric 211 is chosen such that it will emit Cherenkov radiation 213 when irradiated by the therapeutic radiation source. Suitable materials for the optically transmissive dielectric 211 include transparent plastics, such as polymethyl methacrylate, PMMA, or a polycarbonate, or any other suitable polymer, or glass, including glass in fibre form, or water-based materials. When the patient is irradiated by the beam of therapeutic radiation 203, the patient 207 may also emit low levels of Cherenkov radiation 215 due to at least the outermost portions of their epidermis/dermis acting as a optically transmissive dielectric.

Cherenkov radiation 213, 215 will typically be within the visible and/or ultraviolet wavelength range.

A light detector 217 is positioned to detect Cherenkov radiation from either or both of the patient 207 and the optically transmissive dielectric 211. A greater thickness or volume of the optically transmissive dielectric 211 will produce a greater quantity of Cherenkov radiation. The thickness or volume of the optically transmissive dielectric 211 may be chosen in order to produce a minimum quantity of Cherenkov radiation that is detectable at the light detector 217, or to produce a greater quantity of Cherenkov radiation if desired. Although one detector is described herein, it will be appreciated that multiple detectors, or an array of detectors, may be used. The multiple detectors may be spaced apart. Such an arrangement will be beneficial in circumstances in which the patient could obscure the view of the Cherenkov radiation from a single detector, for example, if the therapeutic radiation source 201 and the optically transmissive dielectric 211 were positioned below the patient 207 and the light detector 217 were positioned above the patient 207. Adding at least an additional detector allows Cherenkov radiation from throughout the patient receiving space to be detected. Likewise, the optically transmissive dielectric 211 may be positioned such that any Cherenkov radiation produced will not be obscured by the patient, such as by arranging the optically transmissive dielectric 211 and the light detector 217 closer to the therapeutic radiation source 201 than the patient is positioned. The light detector may be an optical camera. The light detector may be a closed-circuit television, CCTV, camera, that is also used to film/record and/or monitor the subject or patient 207.

The therapeutic radiation source 201 is mounted on a rotatable gantry 219 and is rotatable about the patient receiving space 205. In some cases, the light detector 217 may also be mounted on the gantry 219 and can be rotated with the therapeutic radiation source 201 as the therapeutic radiation source 201 rotates about the patient receiving space 205 during radiotherapy or calibration procedures.

The therapeutic radiation source 201 may be attached to, mounted on, or contained at least partly within a housing 221. The optically transmissive dielectric 211 may be arranged such that it forms part of the housing 221. The housing 221 may form a bore in the form of a hollow cylindrical space that is surrounded by the housing. The gantry 219 is arranged such that any component on the gantry, such as the therapeutic radiation source 201, is circumferentially rotatable about the bore. The therapeutic radiation source 201 is arranged to emit therapeutic radiation in a direction that extends from the circumference of the bore inwards. The bore may have a substantially cylindrical surface within the housing, the surface defining the outer limits of the hollow, and at least one open end via which a patient or other matter can enter the bore. The hollow space of the bore extends from the open end of the bore into the housing. The patient 207 and patient support surface 209 can be moved into and out of the bore as indicated by arrow A-B in FIG. 2. The bore therefore can form at least part of the patient receiving space 205 so that directing therapeutic radiation towards the bore also directs radiation towards the patient receiving space 205. The optically transmissive dielectric 211 may be disposed on the cylindrical surface of the bore, for example so as to form part or all of a cylindrical inner surface (as shown in FIG. 2).

The system 200 is located within a room that is illuminated by an illumination source 223. The illumination source 223 will typically be a light emitting diode, LED, based light source. The illumination source 223 emits light having wavelengths in the visible range, such as between 410 and 760 nanometres. The illumination source 223 may comprise a single light emitting diode or multiple light emitting diodes. In one example, each of multiple light emitting diodes emits light with a different wavelength range, for example, there may be a diode that emits blue light, a diode that emits red light, and a diode that emits green light. The output of each diode is combined to form an effective white light source. The illumination source 223 may combine light emitting diodes with other components, such as a phosphor element, to provide white light illumination.

The system 200 also comprises a quality assurance module 225. Although shown as a physical entity in FIG. 2, the quality assurance module 225 may be embodied in software only. The detector 217 is configured to transmit a signal based on the detection of Cherenkov radiation to the module 225. The quality assurance module 225 is configured to process the signal in order to estimate parameters related to radiotherapy quality assurance. Examples of such parameters include an assessment of the dose received by the patient, for patient dose monitoring or dose evaluation purposes, and an assessment of the dose delivered during a calibration routine, for calibration purposes. For example, the radiation dose received by the patient in units of grays or sieverts will be proportional to the amount of Cherenkov radiation produced/detected and can be estimated or assessed accordingly. Although measuring the amount of Cherenkov radiation is not a direct measure of dose energy per unit volume, which can be directly measured using a calorimeter, the output radiotherapy beam of a particular linac can be calibrated such that the proportionality of the Cherenkov radiation to dose can be established. It is also important to note that there is no Cherenkov radiation produced from the low energy part of the radiotherapy beam spectrum and an estimate based on Cherenkov radiation will preferentially measure the primary beam, rather than the scatter.

A computer-based system 227 may be used for controlling or operating various parts of the system 200. The computer-based system comprises a computer-readable medium 229 containing instructions that, when executed by a processor, cause the system to perform any of the methods described herein.

The optically transmissive dielectric 211 may alternatively, or additionally, be disposed outside of the space enclosed by the bore or as a separate component within the space enclosed by the bore. The patient support surface, or table, 209, which may be equivalent to the patient support surface 114, may be made at least partially of a optically transmissive dielectric material—thereby giving the patient support surface dual functionality and obviating any need for the system to have a separate component to provide the functionality of the optically transmissive dielectric. In each of these examples, the therapeutic radiation source 201 is arranged to provide therapeutic radiation 203 to irradiate both the patient and the optically transmissive dielectric. In some examples, the optically transmissive dielectric may be absent, and in those examples the therapeutic radiation source 201 is configured simply to irradiate the patient. In some examples, the patient may be absent, and in those examples the therapeutic radiation source 201 is configured simply to irradiate the optically transmissive dielectric.

In each of FIG. 3 to FIG. 8 below, a patient 207 is shown, but the system may also function in the absence of a patient.

In each of the examples of FIG. 3 to FIG. 8 below, the Cherenkov radiation produced by the beam of therapeutic radiation 203 may be measured before the beam of therapeutic radiation 203 enters the patient and/or after the beam of therapeutic radiation 203 passes through the patient. In each of the examples of FIG. 3 to FIG. 8 below, the optically transmissive dielectric may be arranged such that Cherenkov radiation is produced before the beam of therapeutic radiation 203 enters the patient and/or it may be arranged such that Cherenkov radiation is produced after the beam of therapeutic radiation 203 enters the patient.

FIG. 3 shows a cross-section of part of the system 200 showing the arrangement in which the optically transmissive dielectric 211 is disposed on the cylindrical inner surface of the bore, as shown in the perspective view of FIG. 2. Alternatively or additionally, the equipment cover itself is made out of the dielectric material. For example, the internal bore surface of the Elekta Unity MR-linac could be made of the dielectric material. Since the beam of therapeutic radiation will always pass through the internal bore surface cover, the cover will emit Cherenkov radiation whenever the beam is on. In FIG. 3, the light detector 217 has been mounted on the rotatable gantry 219, and can rotate about the patient receiving space 205, with the therapeutic radiation source 201, as indicated by arrows A and B.

However, it is also possible to have a detector that is separate/separable from the gantry and is thus in a fixed position relative to the patient receiving space 205. The light detector 217 is arranged to receive Cherenkov radiation 213, 215 from the optically transmissive dielectric 211 and the patient 207. The Cherenkov radiation 213, 215 is shown with arrowheads indicating the direction of emission from the optically transmissive dielectric and patient respectively towards the light detector.

FIG. 4 shows a cross-section of an example of a system 200 in which the optically transmissive dielectric 211 is not positioned on the cylindrical surface of the bore. Instead, the patient support surface 209, in this case a table, is formed of the optically transmissive dielectric material. All or part of the table may be formed from the optically transmissive dielectric material. In this example, the patient support surface 209 will emit Cherenkov radiation 401 when irradiated by the therapeutic radiation beam 203 from the therapeutic radiation source 201 and the light detector 217 is positioned to detect either or both of that Cherenkov radiation 401 and any Cherenkov radiation 215 from the patient 207.

FIG. 5 shows a cross-section of an example of a system 200 in which a optically transmissive dielectric 501 is arranged as a separate component within the bore. The optically transmissive dielectric 501 may be one piece of material or multiple pieces of material that are arranged in order to emit Cherenkov radiation 503 when irradiated by a beam of therapeutic radiation 203. The multiple pieces of material may be spaced radially apart to enable the production and detection of Cherenkov radiation from multiple rotational positions of the gantry.

The one or more pieces of material that form the optically transmissive dielectric 501 do not need to be formed in a particular shape. In some examples, the optically transmissive dielectric 501 is a thin and flat sheet of material that is placed normal to the beam. Such a sheet would intercept very little of the primary treatment beam and the Cherenkov radiation 503 observed from the sheet would represent the fluence of the radiation beam delivered.

In some examples, the optically transmissive dielectric 501 is divided into multiple sub-elements that allow the separate detection of various regions of the beam of therapeutic radiation 203. The sub-elements may take the shape of a series of rods or an array of fibre optic components. Such an approach allows spatial resolution to be realised by detecting Cherenkov radiation element by element, rather than, for example, by direct viewing on a camera of a larger area.

Such an approach can be advantageous for measuring Cherenkov radiation from difficult to view areas, such as the inside of the bore.

FIG. 6 shows a cross-section of an example of a system 200 in which a optically transmissive dielectric is arranged outside of the bore itself. An additional cylindrical component 601, for example an MR apparatus 112, may lie between the therapeutic radiation source 201 and the bore or patient receiving space 205. A optically transmissive dielectric 603 can be likewise arranged such that it lies between the radiation source and the bore but is outside of the bore itself, for example, the optically transmissive dielectric 603 may form part of the housing 221. The optically transmissive dielectric 603 may form part of the additional cylindrical component 601, or alternatively, may be separate to the additional cylindrical component 601. The optically transmissive dielectric 603 can be mounted such that it rotates with the gantry 219 and therapeutic radiation source 201, or it can be fixed such that it does not rotate with the gantry 219. The optically transmissive dielectric 603 may be one piece of material or multiple pieces of material, as in the example of the optically transmissive dielectric 501 above. The optically transmissive dielectric 603 is positioned so that when the therapeutic radiation source 201 emits a beam of therapeutic radiation 203 towards the patient receiving space 205, the optically transmissive dielectric 603 is irradiated in order to cause it to emit Cherenkov radiation FIG. 7 shows a cross-section of an example of a system 200 with the addition of a wavelength shifter component 701. The wavelength shifter component 701 is positioned next to a optically transmissive dielectric 705, which could take the form of any of the optically transmissive dielectric configurations disclosed herein.

Alternatively, the wavelength shifter component 701 may be arranged about the bore and spaced apart from the optically transmissive dielectric 705. When the optically transmissive dielectric 705 is irradiated by therapeutic radiation 203 from the radiation source 201, it emits Cherenkov radiation 707. The Cherenkov radiation 707 is incident on the wavelength shifter component 701, which absorbs the Cherenkov radiation 707 and emits photons 709 at a different wavelength to that of the Cherenkov radiation, effectively converting, or shifting, the Cherenkov radiation from one wavelength to another wavelength. Cherenkov radiation produced by the patient 207 during radiotherapy will also be converted by the wavelength shifter component 701 if the wavelength shifter component 701 is positioned to receive it. A benefit of converting the radiation in this way is that, compared to the Cherenkov radiation 707, the photons 709 may be more easily, or preferentially, detected against a background of room illumination. For example, the wavelength shifter component material may be chosen such that the wavelength of its emitted photons is preferentially detected by the light detector 217 with better signal to noise ratio than that of the detection of Cherenkov radiation by the detector 217. Although the light detector 217 is not shown as mounted on the gantry 219 in FIG. 7, the light detector 217 may be mounted on the gantry in other examples. In one example, the wavelength shifter component 701 comprises an organic or plastic material, such as a PMMA-based material or polyvinyltoluene-based material. In one example, the wavelength shifter component 701 is an inorganic crystalline material. The wavelength shifter component 701 may also be referred to as a scintillator component and may function through the process of scintillation.

FIG. 8 shows the system of FIG. 7 with an additional fibre optic component 803. In FIG. 8, the converted photons 709 are transmitted by the fibre optic component 803 to the light detector 217. The fibre optic component 803 may also or alternatively be used to transmit Cherenkov radiation to the light detector 217 from at least one of the optically transmissive dielectric 705 and the patient 207. In some examples the fibre optic component 803 is used without the wavelength shifter component 701. The fibre optic component 803 may itself produce Cherenkov radiation. The use of the wavelength shifter component 701 to convert Cherenkov radiation from the optically transmissive dielectric 705 or the patient 207 into converted photons 709 can advantageously separate Cherenkov radiation produced by the patient or the optically transmissive dielectric from Cherenkov radiation produced by the fibre optic component 803 itself—thereby avoiding accuracy degradation that would otherwise be caused by Cherenkov radiation that is emitted from the fibre optic component 803.

In one example, one or more wavelength shifter components have Cherenkov radiation transmitted to them through fibre optic components. In such a case the fibres would produce a small amount of Cherenkov radiation, but the amount falling within the range of angles that can be propagated within the fibre is expected to be small.

The fibre optic component 803 can be designed to preferentially transmit photons at the wavelength of the converted photons 709, or alternatively, the wavelength shifter component material may be chosen to match the transmission properties of the fibre optic. In FIGS. 7 and 8, the light detector 217 is not mounted on the gantry, however, in some examples it may be. A bundle of optical fibres with suitable properties may be used. The one or more fibres of such a bundle may be arranged such that their aperture intersects the direction of the Cherenkov radiation, or the converted photons 709, or both. Appropriate optical coupling components, such as a lens, can be used to improve the collection of Cherenkov radiation, or converted photons, or both, by the one or more fibres. A high density bundle of fibre optic components can be used to measure the radiation fluence distribution with a relative range of up to one part in several thousand.

FIG. 9 shows a method 900 that can be performed with the system 200. At step S901, a therapeutic radiation source 201 is used to irradiate a optically transmissive dielectric with therapeutic radiation. The optically transmissive dielectric can be configured according to any of the examples disclosed herein. At step S902, a light detector 217 is operated to detect Cherenkov radiation emitted by the optically transmissive dielectric consequent to the emission of therapeutic radiation by the therapeutic radiation source 201. Such a method may be performed in the absence of a patient in the patient receiving space, such as for calibration purposes, or with a patient present and undergoing radiotherapy. If a patient is present, the method may be performed before and/or after the therapeutic radiation passes through the patient. The method may further comprise producing a signal at the light detector 217 based on the detected Cherenkov radiation, transmitting the signal to a radiotherapy quality assurance module 225, and processing the signal at the module 225. Such processing may be performed for evaluating or estimating the dose delivered to the patient or for calibrating the dose delivery pre- or post-treatment in the absence of a patient. The method 900 may be performed by executing instructions contained on a computer-readable medium.

FIG. 10 shows a system 1000 for improved detection of Cherenkov radiation produced during radiotherapy. The system 1000 may be used with the system 200 of FIG. 2. A control module 1001 is arranged to supply a signal to a therapeutic radiation source 1003. The therapeutic radiation source 1003 may be equivalent to the therapeutic radiation source 201 of FIG. 2. The control module 1001 is configured to supply the signal to control, during a radiotherapy or calibration session, therapeutic radiation source 1003 to cause emission of a series of pulses of therapeutic radiation towards the patient receiving space 205 of the system 200. Although shown as a physical entity in FIG. 10, the control module 1001 may be embodied in software only. Each pulse of therapeutic radiation has a duration. In some examples, each pulse in the series has the same duration, and in other examples, they do not. Between adjacent pulses, therapeutic radiation is not emitted by the therapeutic radiation source 1003. There is therefore a series of time periods during which therapeutic radiation is not emitted, which can be described as a series of off periods. In some examples, each off period in the series has the same duration, and in other examples, they do not.

An operation module 1005 supplies a signal to a light detector 1007, which may be the light detector 217 of system 200. The operation module 1005 is configured to operate the light detector 1007 to detect Cherenkov radiation during a series of detection windows, wherein each detection window corresponds to a respective one of the series of pulses of therapeutic radiation that the control module 1001 causes the therapeutic radiation source 1003 to emit. The operation of the light detector is timed so that Cherenkov radiation emitted as a consequence of the respective pulse of therapeutic radiation is detected by the light detector during a least a part of that detection window. In other words, the control of the emission of therapeutic radiation and the operation of the detector to detector Cherenkov radiation are in phase with one another.

Additionally, the operation module 1005 operates the light detector so that, between adjacent detection windows, the light detector is not able to detect Cherenkov radiation. The light detector therefore is operated to have a series of off periods that is in phase with the series of off periods of the therapeutic radiation source. For example, the operation module may provide an electronic gating signal to the light detector such that its detection capability pulses on and off to form a series of detection windows. Alternatively, or additionally, the light detector may be operated using a shutter that moves to block light from reaching a sensor of the detector between detection windows, and moves to allow light, including Cherenkov radiation, to reach the sensor during detection windows. Such a switching effect can be achieved through electronic, mechanical, optical, or software-implemented means.

In addition, the system 1000 may be arranged to control room lighting sources such as the illumination source 223 of FIG. 2, which in one example is LED-based. The illumination source may be controlled in a similar pulsed manner to that of the therapeutic radiation source 1003 and the light detector 1007, timed such that pulses of illumination are emitted by the illumination source in between adjacent detection windows of the light detector. Providing that the pulses are of sufficiently high frequency (for example above 50 Hz) they will appear to the human eye as continuous illumination. A driving circuit for the LED is arranged so that the LEDs are always pulsed out of phase with the detection windows of the light detector. This arrangement ensures that, aside from Cherenkov radiation, the room is dark to the light detector during radiation detection but appears to be normally lit to the patient in the room. The system 1000 will also advantageously improve the signal to noise ratio of Cherenkov radiation detected in dark room conditions. Similarly, in examples where a separate video monitor, such as a CCTV camera, is used to monitor the patient, the video monitor may be controlled by system 1000 to record images in a series of pulses, the timing and duration of those pulses being in phase, matched, or synchronised, to the pulsing of the illumination source 223, in order to remove the effects of illumination strobing from the patient monitoring footage.

Usually, the intensity of Cherenkov radiation is so weak that it is not detectable against a concurrent background of conventional room lighting. However, the approaches disclosed herein advantageously allow Cherenkov radiation to be detected despite apparently concurrent room lighting. The approaches enable Cherenkov radiation to be used as a measure for radiotherapy quality assurance while simultaneously retaining the benefits of illuminating the treatment room and/or patient.

FIG. 11 shows a timeline with exemplary control and operation pulses produced by the system 1000 of FIG. 10 for each of the radiation source 1003, light detector 1007, illumination source, and video monitor. Lines A and B define a time window. Before the window begins at time A, the illumination source and video monitor have been turned off by the system 1000, meaning that illumination is not being emitted and video is not being recorded. At the start of the window, marked by line A, the radiation source and light detector are turned on by the system 1000. During the window, between lines A and B, therapeutic radiation is emitted by the therapeutic radiation source 1003 and subsequent Cherenkov radiation produced by either the optically transmissive dielectric 211 or the patient 207 is detected at the light detector 1007. At the end of the window, marked by line B, the radiation source and light detector are turned off. After the window, the illumination source and video monitor are turned on while the therapeutic radiation source and the light detector remain off.

The various operations during and adjacent to the exemplary time window between A and B repeat to form a series of pulses.

Although square pulses of regular frequency are depicted, any pulse shape may be used. For example, pulses may be produced with rounded edges, or a sawtooth profile. Moreover, the pulse occurrence need not be regular or with any particular frequency.

In some examples, the duration of each pulse of radiation and the duration of each detection window are the same, as is the rate at which they occur. For example, each of the pulse duration and the detection window may last for a duration that is less than the time between adjacent illumination pulses for a source operating at 50 Hz, for example between 0.2 and 0.1 seconds. The duration of each pulse may be determined based on the properties of the light detector, such as frame rate. For example, for a frame rate of 25 frames per second, a pulse duration of around 40 ms may be used. For a frame rate of 120 frames per second, a pulse duration of around 8 ms may be used. The duration or frequency of each pulse of radiation may be determined according to emission at a pulse recurrence frequency, PRF, of the radiation source, and the light detector may be operated to provide detection windows at the same frequency, or with the same phase. Alternatively, the control and operation of each apparatus by the system 1000 may be in-phase but with different frequency, such as by controlling the radiation source to emit at the PRF, and operating the light detector to detect at an integer multiple or fraction of that frequency, such as by operating it at a frequency that is half the PRF. Moreover, although the example of FIG. 11 has been described in terms of the light detector being pulsed on and off at times that coincide with the radiation source being pulsed on and off, there may be a phase difference between the pulse on times and/or the pulse off times of the therapeutic radiation source and the light source. For example, Cherenkov radiation will only occur after the therapeutic radiation source has been turned on and so the light detector may be pulsed on a short time after the therapeutic radiation source has been pulsed on.

The system 1000 may be operated through use of a computer-readable medium, such as computer-readable medium 229, containing instructions that, when executed by a processor, cause the system to perform methods described herein. The computer-readable medium may be a component of the system 1000. The computer-readable medium, or system 1000 itself, may be a component of the computer system 227.

FIG. 12 shows a method 1200 for implementation in the system 1000. At step S1201, the control module 1001 controls, during a radiotherapy or calibration session, the therapeutic radiation source in a manner that causes the emission of a series of pulses of therapeutic radiation towards the patient receiving space. At step S1203, the operation module 1005 operates a light detector to detect Cherenkov radiation during a series of detection windows, and at step S1205, the operation module 1005 operates the light detector so that, between adjacent detection windows, the light detector is not able to detect Cherenkov radiation. The method is implemented using one, or a combination, of the examples of operation described for the system 1000 above.

FIG. 13 shows a light detector 1300 for detecting Cherenkov radiation according to an example of the disclosure. The light detector 1300 may be used as the light detector 217 in the system 200 of FIG. 2 or as the light detector 1007 operated by the system 1000 of FIG. 10. The light detector 1300 is shown in a first configuration A and a second configuration B. The light detector 1300 comprises a sensor 1301 configured to detect photons of Cherenkov radiation. The sensor 1301 produces an electrical signal based on detected photons. In one example, the sensor 1301 is that of a digital camera, and/or may be a CCD-based (Charge coupled Device) or a CMOS-based (Complementary metal-oxide-semiconductor) sensor. The light detector 1300 has an aperture 1303 that allows light to enter the detector and reach the sensor. The light detector 1300 also comprises a shutter, shown in FIG. 13 as a mechanical shutter 1305. When the mechanical shutter 1305 is in a first, open, position, as shown for the light detector in the first configuration A, the aperture 1303 is unobscured and light 1307, in this case photons of Cherenkov radiation, is able to reach the sensor 1301 and be detected. The mechanical shutter 1305 is movable to a second position, shown in the second configuration B, that covers the aperture 1303 and prevents light 1309 from reaching the detector sensor 1301. The light 1309 shown as incident on the second configuration B may be emitted by the room illumination source, such as an LED, or it may be a combination of room illumination with Cherenkov radiation produced by the radiotherapy system. The mechanical shutter can be controllably and repeatedly moved between the position shown in the first configuration A, in which light 1307 is able to reach the sensor 1301, and the position shown in the second configuration B, in which light 1309 is blocked by the shutter 1305 from reaching the sensor 1301.

In this way, the mechanical shutter 1305 allows the light detector 1300 to be operated in a manner described by the system 1000 of FIG. 10 and the method 1200 of FIG. 12. The operation module 1005 operates the light detector 1300 in accordance with the steps S1203 and S1205 of the method of FIG. 12. As shown in the example of FIG. 11, by linking the movement of the shutter to the operation of the radiation source and room illumination, the light detector 1300 can be operated to preferentially detect Cherenkov radiation and block light from the illumination source. For example, moving the shutter to the open position, as in the first configuration A, turns the detector on. Closing the shutter, as in the second configuration B, turns the detector off. The detector can therefore be switched between on and off states in a pulsed manner. The system allows Cherenkov radiation to be detected for radiotherapy quality assurance without having to perform radiotherapy with the patient a dark room.

The switching effect of the shutter can be achieved through electronic, mechanical, optical, or software-implemented means. In some examples, an electrical shutter mechanism may be used in place of the mechanical shutter 1305. The electrical shutter may function through, for example, switching between collecting signals generated at the sensor 1301 when 'on' and not collecting signals generated at the sensor 1301 when 'off'. Similarly, other types of mechanical shutter may be used, and the shutter need not be integrated into the detector itself but may be placed anywhere that allows it to block light that would otherwise be incident on the detector.

FIG. 14 shows another example detector that allows Cherenkov radiation to be detected for radiotherapy quality assurance without having to perform radiotherapy with the patient in a dark room. Detector 1300 may be provided with a filter component 1401. The filter acts to block or remove light of certain wavelengths and to pass light of other wavelengths. Although FIG. 14 shows the light detector 1300 with the mechanical shutter 1305, in other examples the shutter 1305 may be absent.

The filter component 1401 is arranged in front of the detector such that light is incident on the filter component before it would otherwise be incident on the detector. The filter component is arranged such that Cherenkov radiation 1307 is substantially passed by the filter component. Light 1309 from other sources, such as light from illumination sources in the room, such as the LED-based illumination source 223, is blocked by the filter component 1401 and does not pass to the sensor 1301. Only the substantially unfiltered Cherenkov radiation, 1307, is passed to the sensor 1301.

The light detector 1300 with the filter component 1401 may be used with examples disclosed herein in which the light detector is operated with a shutter in a pulsed manner. In particular, further improvements to the signal-to-noise ratio of detected Cherenkov radiation may be achieved by combining the shutter 1305 and the filter component 1401 with the system 1000 or method 1200. However, the example of FIG. 14 need not necessarily be used in combination the pulsing systems and methods disclosed herein. The example of FIG. 14 separates the Cherenkov radiation from other light sources by wavelength, allowing Cherenkov radiation to be detected for radiotherapy quality assurance without requiring the patient to undergo radiotherapy in a dark room.

The filter component 1401 may comprise a narrow band, or notch filter, and may be particularly be suited for use with narrow-band LEDs of known spectrum, and in particular for blue LEDs. Although Cherenkov radiation is biased towards blue light, it is relatively broad band, and so a narrow range of blue wavelengths from an LED can be blocked without substantially preventing the detector from detecting Cherenkov radiation. The filter may be an optical filter, such as those based on optical interference, chosen to have an appropriate bandwidth and transmission range. In some examples, the filter is a thin-film, or dichroic filter, comprising alternating layers of optical coatings with different refractive indices.

FIG. 15 shows the effect of the filter component 1401 on the incident spectrum of light of each of the Cherenkov radiation 1507 and the room illumination 1509. The room illumination 1509 spectrum will typically be well-known and may be very precisely defined in the example of an LED-based illumination source. A graph 1500A shows a spectrum of Cherenkov radiation 1507A and a spectrum of room illumination 1509A. The two spectra overlap in a particular wavelength range 1511. Choosing a filter component 1401 that removes wavelengths of light in an appropriate filter range 1511 allows the room illumination to be at least partially filtered out. A detector is chosen with a wavelength detection range 1513. As shown in 1500B, after the filter component 1401 removes the wavelengths within the filter range 1511, the detector with the detector range 1513 only sees Cherenkov radiation 1507B that has been passed by the filter. The room illumination 1509B passed by the filter does not have a wavelength component within the detection range of the detector. Although some of the Cherenkov radiation may be affected, blocked, or modified by the filter component 1401, such an approach allows most of the Cherenkov radiation through while removing room illumination, allowing the Cherenkov radiation produced during radiotherapy to be imaged without needing the patient to be kept in the dark. The signal-to-noise ratio of Cherenkov radiation detection can also be improved, particularly if the filter 1401 is used in combination with other systems and methods disclosed herein, such as a mechanical shutter operated in a pulsed manner.

The filter range 1511 and the detector range 1513 are chosen according to the spectra 1507A and 1509A. In one example, the filter may remove light of all wavelengths higher than a particular wavelength, where the particular wavelength corresponds to a high intensity of Cherenkov radiation and low intensity of room illumination. For example, the filter component 1401 may block all wavelengths within the filter range 1511 as well as wavelengths greater than that range, effectively blocking all room illumination. Such an approach allows optical detectors with a much wider range than the detector range 1513 to be used to detect Cherenkov radiation against a background of room illumination. For example, a standard digital camera or CCTV camera may be used. In one example, the filter range 1511 is within the visible wavelength range, between 410 to 760 nanometres. The room illumination 1509 spectrum may lie within the same range of between 410 to 760 nanometres. The room illumination 1509 spectrum may have a particularly high intensity between 410 nm and 500 nm with an intensity peak at a wavelength of approximately 450 nm. As Cherenkov radiation is typically within the visible or ultraviolet wavelength ranges, the detector range 1513 may span at least the range of 300 to 750 nanometres. In some examples, the Cherenkov radiation has wavelengths within the range of about 380 nm to 500 nm. In some examples, the Cherenkov radiation has wavelength components within the visible and/or ultraviolet range and the filter component 1401 blocks wavelengths greater than about 450 nm.

A method can be performed in the system of FIG. 14 to improve the detection of Cherenkov radiation at a light detector. Firstly, a light source 223 is used to provide illumination in the room in which a radiotherapy system 200 is located. The therapeutic radiation source 201 of the radiotherapy system is used to emit therapeutic radiation. Cherenkov radiation 1307 produced as a consequence of that emission is received by a filter component 1401, which is configured as described above, and a light detector is used to detect light passed by the filter. The method may be combined with the method steps described by FIG. 9 and/or the method steps of FIG. 12 in order to further enhance detection of Cherenkov radiation.

In other examples, the filtering by wavelength may be performed electronically or through software.

FIG. 16 shows a transverse cross-section of part of the system 200 showing an arrangement whereby Cherenkov radiation is produced at multiple locations in the system.

The therapeutic radiation source 201 emits the beam of therapeutic radiation 203 toward the patient receiving space 205. Before the beam of therapeutic radiation 203 reaches the patient receiving space 205 or the patient 207, it passes through a region labelled X in FIG. 16 and creates Cherenkov radiation. The region labelled X is situated within the optically transmissive dielectric 211, which in this example is disposed on the cylindrical inner surface of the bore. The Cherenkov radiation from the optically transmissive dielectric 211 at the region X can then be detected or measured in order to determine properties of the beam of therapeutic radiation 203 as it enters the patient receiving space 205 and before the therapeutic radiation interacts with the patient 207.

The beam of therapeutic radiation 203 passes through the region X and is incident on the patient 207. Radiation that is not absorbed by the patient is then incident on the patient support surface 209. The region labelled P in FIG. 16 relates to a region of the patient 207 subjected to the therapeutic radiation. As explained above, tissue of the patient 207 may also emit Cherenkov radiation in response to being subjected to the therapeutic radiation. Hence, the region P represents a source of Cherenkov radiation emitted by the patient.

Therapeutic radiation that passes through the patient 207 will pass into a region Y of the patient support 209. The patient support surface 209 comprises an optically transmissive dielectric (as described in the example of FIG. 4 above) and so Cherenkov radiation is produced in the region Y.

After passing through the patient support surface 209, the beam of therapeutic radiation 203 exits the bore of the radiotherapy system 200 by again passing through the optically transmissive dielectric 211 that is disposed on the cylindrical inner surface of the bore. The region in which that occurs is labelled with a Z in FIG. 16. Although the region Z and the region X are both located within the optically transmissive dielectric 211, each region is located on either side of the patient receiving space and so, due at least to patient absorption and beam divergence of the therapeutic radiation, will experience differing amounts and distributions of radiation.

Cherenkov radiation can therefore be produced at four regions in the system of FIG. 16: X, Y, Z, and P. However, in some examples, some of the optically transmissive dielectric is omitted and so Cherenkov radiation is not produced at all four regions and is instead merely produced at one or more of the four regions. In some examples, Cherenkov radiation from region Y and region Z is measured. In some examples, Cherenkov radiation from only one of region Y and region Z is measured. In some examples, Cherenkov radiation from region X is measured in addition to Cherenkov radiation from region Y and/or region Z. In each example, Cherenkov radiation from region P may optionally, additionally, be measured.

In some examples, the optically transmissive dielectric component that contains the region X and/or the region Z may not form part of the cylindrical inner surface of the bore and may instead be disposed elsewhere in the system. The optically transmissive dielectric can be located anywhere such that region X and region Z are located either side of the patient receiving space 205 or the patient 207. In some examples, region X and region Z may in fact be located within separate optically transmissive dielectric components that are located either side of the patient receiving space 205 or the patient 207.

Cherenkov radiation from each or all of the regions may be detected using detecting apparatus such as the detectors and cameras disclosed herein. A single camera or detector may be used to detect Cherenkov radiation from multiple regions, or, alternatively, multiple cameras or detectors may be used in combination—for example one per region. In some examples, the one or more detectors are in fixed position relative to the regions to be measured, and do not rotate with the gantry 219. In other examples, the one or more detectors are rotatable and/or may be mounted to the gantry 219. Using the gantry to rotate the one or more detectors around the patient 207 enables a three dimensional reconstruction of the beam of therapeutic radiation 203 to be obtained, using a technique analogous to computed tomography.

Measuring Cherenkov radiation emitted from before it passes through the patient receiving space (region X) gives an indication of the beam of therapeutic radiation 203 at the source of the beam. As described above, such a measurement can be used to determine the shape of the beam of therapeutic radiation 203 on entry to the patient receiving space. Each of the region Y and the region Z provide a measurement of the beam of therapeutic radiation 203 after it has passed through the patient 207, which can be used to measure the interaction of the beam with the patient 207. That can give an indication of whether the beam is shaped correctly and/or how accurate the patient model is within the treatment planning system, and/or whether the patient is correctly positioned. For example, if the patient position is different to that intended, either due to the patient moving or due to inaccuracy in the patient model in the treatment planning system, then the beam shape and intensity, as determined by measuring Cherenkov radiation from the location Y or the location Z, will differ from the beam shape that is expected or predicted. Furthermore, information obtained from measuring Cherenkov radiation produced from region Y and/or region Z can also be used in calibrating the beam of therapeutic radiation 203. For example, the intensity, direction, and/or collimation of the beam of therapeutic radiation 203 may be adjusted accordingly. In some examples, and as described above, the detecting apparatus can comprise an array or detectors and can determine a spatial distribution of the beam of therapeutic radiation 203, which may likewise be adjusted through calibration.

Measurement of Cherenkov radiation from the region X and at least one of the regions Y and Z provides additional information compared to a measurement of Cherenkov radiation merely from one region. For example, a comparison can be made between the properties of the therapeutic radiation upon entry to the bore (at region X) and the properties of the therapeutic radiation upon exit from the bore (at region Y or Z), or after it has passed through the patient. This comparative approach can improve the accuracy of each of the capabilities described above without requiring significant amounts of additional componentry. Such a comparison may be made by using data or image processing techniques such as a performing a subtraction of the Cherenkov radiation detected upon beam entry from the Cherenkov radiation detected upon beam exit.

Measurement of Cherenkov radiation emitted by the patient (region P) can provide supplementary information relating to the dose delivered to the patient.

It will be appreciated that in some examples, the beam direction may be inverted and the beam of therapeutic radiation 203 will be directed such that it passes through the region Z, followed by the region Y, followed by the region P, followed by the region X. Such an arrangement can also be used as described herein, with a measurement of Cherenkov radiation from the region X used to represent the beam of therapeutic radiation 203 after it has passed through the patient, and a measurement of Cherenkov radiation from at least one of the region Z and/or Y used to represent the beam of therapeutic radiation as it enters the patient receiving space 205.

In FIG. 16, a patient 207 is shown, but the system may also function in the absence of a patient.

Systems and methods are provided for detecting Cherenkov radiation produced during radiotherapy. A radiotherapy system comprises a patient receiving space for receiving a patient, a therapeutic radiation source, and a light detector configured to detect Cherenkov radiation subsequent to the emission of therapeutic radiation. Optionally, the system may make use of a optically transmissive dielectric to produce Cherenkov radiation.

It should be understood that, in the present disclosure, the verb 'to operate' may be used to mean 'to execute' or 'to run'.

Those skilled in the art will recognise that a wide variety of modifications, alterations, and combinations can be made with respect to the above described examples without departing from the scope of the disclosed concepts, and that such modifications, alterations, and combinations are to be viewed as being within the ambit of the disclosed concepts.

Those skilled in the art will also recognise that the scope of the invention is not limited by the examples described herein, but is instead defined by the appended claims.

The various methods described above may be implemented by a computer program. The computer program may include computer code arranged to instruct a computer to perform the functions of one or more of the various methods described above. The computer program and/or the code for performing such methods may be provided to an apparatus, such as a computer, on one or more computer-readable media or, more generally, a computer program product. The computer-readable media may be transitory or non-transitory. The one or more computer-readable media could be, for example, an electronic, magnetic, optical, electromagnetic, infrared, or semiconductor system, or a propagation medium for data transmission, for example for downloading the code over the Internet. Alternatively, the one or more computer-readable media could take the form of one or more physical computer-readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

In an implementation, the modules, components and other features described herein can be implemented as discrete components or integrated in the functionality of hardware components such as ASICS, FPGAs, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware component may be or include a special-purpose processor, such as a field programmable gate array (FPGA) or an ASIC. A hardware component may also include programmable logic or circuitry that is temporarily configured by software to perform certain operations.

Accordingly, the phrase "hardware component" should be understood to encompass a tangible entity that may be physically constructed, permanently configured (e.g., hardwired), or temporarily configured (e.g., programmed) to operate in a certain manner or to perform certain operations described herein.

In addition, the modules and components can be implemented as firmware or functional circuitry within hardware devices. Further, the modules and components can be implemented in any combination of hardware devices and software components, or only in software (e.g., code stored or otherwise embodied in a machine-readable medium or in a transmission medium).

There is described a computer-readable medium comprising computer-readable instructions which, when executed by a processor, cause the processor to perform any of the methods described herein. The computer-readable medium may be a tangible and/or non-transitory medium.

The invention claimed is:

1. A system comprising:
a control module configured to control, during a radiotherapy or calibration session, a therapeutic radiation source to cause emission of a series of pulses of therapeutic radiation towards a patient receiving space;
an operation module configured to:
operate a light detector to detect Cherenkov radiation during a series of detection windows, wherein each detection window corresponds to a respective one of the series of pulses of therapeutic radiation and is timed so that Cherenkov radiation emitted as a consequence of the respective one of the series of pulses of therapeutic radiation is detected by the light detector during a least a part of that detection window; and
operate the light detector so that, between adjacent detection windows, the light detector is not able to detect Cherenkov radiation;
the system further comprising:
an optically transmissive dielectric, wherein the optically transmissive dielectric is arranged such that, when a patient is received in the patient receiving space, both the patient and the optically transmissive dielectric are irradiated by the therapeutic radiation source.

2. The system of claim 1, wherein the control module is further configured to:
control an illumination source to cause emission of a series of pulses of illumination, wherein each pulse of illumination occurs between respective adjacent detection windows.

3. The system of claim 1, wherein a duration of each detection window is within a range of 8 milliseconds to 40 milliseconds.

4. The system of claim 1, wherein controlling the therapeutic radiation source and operating the light detector is performed at a pulse recurrence frequency, PRF, of the therapeutic radiation source.

5. The system of claim 1, wherein the light detector comprises a shutter arranged to move between a first position wherein Cherenkov radiation is receivable by a sensor of the light detector and a second position wherein the shutter substantially prevents light from reaching the sensor.

6. The system of claim 1, wherein the therapeutic radiation source is configured to rotate about the patient receiving space during radiotherapy.

7. The system of claim 1, wherein the light detector is configured to detect light within at least one of a visible wavelength range and an ultraviolet wavelength range.

8. The system of claim 1, wherein at least a portion of the optically transmissive dielectric forms at least a portion of a support for supporting the patient.

9. The system of claim 1, comprising a housing that houses at least a portion of the patient receiving space, and wherein the optically transmissive dielectric forms at least part of the housing.

10. A non-transitory computer-readable medium containing instructions that, when executed by a processor, cause a radiotherapy system to:
control during a radiotherapy or calibration session a therapeutic radiation source to cause emission of a series of pulses of therapeutic radiation towards a patient receiving space;
operate a light detector to detect Cherenkov radiation during a series of detection windows, wherein each detection window corresponds to a respective one of the series of pulses of therapeutic radiation and is timed so that Cherenkov radiation emitted during the respective one of the series of pulses of therapeutic radiation is detected by the light detector during a least a part of that detection window; and
operate the light detector so that between adjacent detection windows, the light detector is not able to detect Cherenkov radiation, wherein the radiotherapy system includes an optically transmissive dielectric, wherein the optically transmissive dielectric is arranged such that, when a patient is received in the patient receiving space, both the patient and the optically transmissive dielectric are irradiated by the therapeutic radiation source.

11. The system of claim 2, wherein the illumination source comprises at least one light emitting diode.

12. The system of claim 2, wherein the control module is further configured to:
control a video camera to record, in a series of recording pulses, wherein each recording pulse is synchronized with a corresponding pulse of illumination.

13. The system of claim 6, wherein the light detector is configured to rotate with the therapeutic radiation source about the patient receiving space during radiotherapy.

14. A method comprising:
controlling, during a radiotherapy or calibration session, a therapeutic radiation source to cause emission of a series of pulses of therapeutic radiation towards a patient receiving space;
operating a light detector to detect Cherenkov radiation during a series of detection windows, wherein each detection window corresponds to a respective one of the series of pulses of therapeutic radiation and is timed so that Cherenkov radiation emitted as a consequence of the respective one of the series of pulses, of therapeutic radiation is detected by the light detector during a least a part of that detection window; and
operating the light detector so that, between adjacent detection windows, the light detector is not able to detect Cherenkov radiation, wherein an optically transmissive dielectric is arranged such that, when a patient is received in the patient receiving space, both the patient and the optically transmissive dielectric are irradiated by the therapeutic radiation source.

15. The method of claim 14, wherein the method is performed in an absence of a patient in the patient receiving space.

16. The method of claim 14, wherein the therapeutic radiation source is configured to rotate about the patient receiving space during radiotherapy.

17. The method of claim 16, wherein the light detector is configured to rotate with the therapeutic radiation source about the patient receiving space during radiotherapy.

18. The non-transitory computer-readable medium of claim 10, wherein the optically transmissive dielectric is a transparent plastic.

* * * * *